US010028838B2

(12) United States Patent
Hodorek et al.

(10) Patent No.: US 10,028,838 B2
(45) Date of Patent: Jul. 24, 2018

(54) AUGMENTED GLENOID COMPONENTS AND DEVICES FOR IMPLANTING THE SAME

(71) Applicant: Tornier, Inc., Bloomginton, MN (US)

(72) Inventors: Brian C. Hodorek, Winona Lake, IN (US); Pierric Deransart, Saint Martin d'uriage (FR); Bradley Grant Emerick, Columbia City, IN (US); Alexandre Terrier, Lausanne (CH); Alain Jean-Pierre Farron, Lausanne (CH); Robert Courtney, Jr., Pierceton, IN (US); Travis James Geels, Fort Wayne, IN (US)

(73) Assignee: Tornier, Inc., Bloomington, MN (US)

( * ) Notice: Subject to any disclaimer, the term of this patent is extended or adjusted under 35 U.S.C. 154(b) by 25 days.

(21) Appl. No.: 14/320,340

(22) Filed: Jun. 30, 2014

(65) Prior Publication Data

US 2015/0374502 A1    Dec. 31, 2015

(51) Int. Cl.
*A61B 17/16* (2006.01)
*A61F 2/40* (2006.01)
*A61B 17/17* (2006.01)

(52) U.S. Cl.
CPC ........ *A61F 2/4081* (2013.01); *A61B 17/1684* (2013.01); *A61B 17/17* (2013.01); *A61B 17/1778* (2016.11); *A61F 2002/4085* (2013.01)

(58) Field of Classification Search
CPC ................................................ A61B 17/1684
See application file for complete search history.

(56) References Cited

U.S. PATENT DOCUMENTS

| 3,559,514 A | 2/1971 | Brownfield |
| 5,203,653 A | 4/1993 | Kudla |
| 5,591,170 A * | 1/1997 | Spievack ............... A61B 17/14 30/122 |

(Continued)

FOREIGN PATENT DOCUMENTS

| DE | 69825973 T2 | 9/2005 |
| EP | 1752105 B1 | 7/2008 |

(Continued)

OTHER PUBLICATIONS

DePuy Synthes. "Global APG—Design Rationale and Surgical Technique." DePuy Synthes, 2010. Web. Dec. 22, 2014. <http://www.synthes.com/sites/NA/NAContent/Docs/Product SupportMaterials/Technique Guides/0612-13-509_GlobalAPGdesignrationaleST.pdf>.

(Continued)

*Primary Examiner* — Zade Coley
(74) *Attorney, Agent, or Firm* — Knobbe Martens Olson & Bear LLP

(57) ABSTRACT

A glenoid component for coupling to a scapula of a subject includes a body. The body includes an articulation surface adapted to articulate with a humeral component, and the body further includes a distal surface adapted to face the glenoid of the scapula. The distal surface includes a base surface portion adapted to face a first portion of the glenoid. The distal surface further includes an augmented surface portion adapted to face a second portion of the glenoid. The base surface portion and the augmented surface portion define an obtuse angle therebetween.

24 Claims, 31 Drawing Sheets

(56) References Cited

U.S. PATENT DOCUMENTS

| | | | |
|---|---|---|---|
| 5,800,551 A | 9/1998 | Williamson et al. | |
| 5,919,195 A * | 7/1999 | Wilson | A61B 17/1666 606/80 |
| 6,699,289 B2 | 3/2004 | Iannotti et al. | |
| 6,949,101 B2 | 9/2005 | McCleary et al. | |
| 7,217,271 B2 * | 5/2007 | Wolford | A61B 17/1666 606/80 |
| 7,473,254 B2 * | 1/2009 | White | A61B 17/1617 606/81 |
| 7,503,921 B2 | 3/2009 | Berthusen et al. | |
| 7,572,259 B2 | 8/2009 | Desarzens et al. | |
| 7,637,909 B2 | 12/2009 | Lechot et al. | |
| 7,749,227 B2 | 7/2010 | Lechot et al. | |
| 7,780,669 B2 | 8/2010 | Lechot et al. | |
| 7,785,329 B2 | 8/2010 | Lechot et al. | |
| 7,803,160 B2 | 9/2010 | Keller | |
| 7,819,875 B2 | 10/2010 | Chana | |
| 7,892,287 B2 | 2/2011 | Deffenbaugh | |
| 7,922,769 B2 | 4/2011 | Deffenbaugh et al. | |
| 7,927,335 B2 | 4/2011 | Deffenbaugh et al. | |
| 8,052,690 B2 | 11/2011 | Berthusen et al. | |
| 8,282,639 B2 | 10/2012 | Chana | |
| 8,475,460 B1 | 7/2013 | Roger et al. | |
| 8,480,674 B1 | 7/2013 | Roger et al. | |
| 8,486,076 B2 | 7/2013 | Chavarria | |
| 8,657,833 B2 | 2/2014 | Burgi et al. | |
| 8,657,834 B2 | 2/2014 | Burgi et al. | |
| 8,721,727 B2 | 5/2014 | Ratron et al. | |
| 8,740,907 B2 | 6/2014 | Penenberg | |
| 8,771,275 B2 | 7/2014 | Xie et al. | |
| 8,834,471 B2 * | 9/2014 | Roger | A61B 17/1664 606/80 |
| 8,864,834 B2 | 10/2014 | Boileau et al. | |
| 9,066,730 B2 | 6/2015 | McMinn et al. | |
| 9,066,731 B2 | 6/2015 | Moore | |
| 9,078,672 B1 | 7/2015 | Rossé | |
| 9,408,652 B2 | 8/2016 | Hassler et al. | |
| 2003/0163135 A1 | 8/2003 | Hathaway | |
| 2003/0220646 A1 * | 11/2003 | Thelen | A61B 17/1642 606/79 |
| 2004/0097947 A1 * | 5/2004 | Wolford | A61B 17/1666 606/80 |
| 2004/0236339 A1 * | 11/2004 | Pepper | A61B 17/164 606/80 |
| 2005/0159751 A1 * | 7/2005 | Berthusen | A61B 17/1624 606/80 |
| 2006/0015110 A1 | 1/2006 | Pepper | |
| 2006/0058809 A1 | 3/2006 | Zink et al. | |
| 2007/0038302 A1 | 2/2007 | Shultz et al. | |
| 2007/0038303 A1 | 2/2007 | Myerson et al. | |
| 2007/0093840 A1 * | 4/2007 | Pacelli | A61B 17/1631 606/80 |
| 2009/0270863 A1 | 10/2009 | Maisonneuve | |
| 2010/0228352 A1 | 9/2010 | Courtney, Jr. et al. | |
| 2011/0004215 A1 * | 1/2011 | Bradley | A61B 17/1684 606/84 |
| 2011/0028977 A1 | 2/2011 | Rauscher et al. | |
| 2012/0109229 A1 | 5/2012 | Forsell | |
| 2012/0123419 A1 | 5/2012 | Purdy et al. | |
| 2012/0239042 A1 | 9/2012 | Lappin et al. | |
| 2013/0144393 A1 | 6/2013 | Mutchler et al. | |
| 2016/0310285 A1 | 10/2016 | Kovacs et al. | |

FOREIGN PATENT DOCUMENTS

| | | | |
|---|---|---|---|
| EP | 2231032 B1 | 8/2011 | |
| EP | 2363098 B1 | 9/2012 | |
| EP | 2626017 A1 | 8/2013 | |
| GB | 2406278 A * | 3/2005 | ......... A61B 17/1615 |
| WO | WO 2005/094693 | 10/2005 | |
| WO | WO 2009/083707 | 7/2009 | |
| WO | WO 2011/012318 | 2/2011 | |
| WO | WO 2014/063197 A1 | 5/2014 | |
| WO | WO 2014063197 A1 * | 5/2014 | ......... A61B 17/1666 |

OTHER PUBLICATIONS

Extended European Search Report issued in EP Appl. No. 15161818.8 dated Nov. 30, 2015 in 6 pages.

Zimmer ®. "Trabecular Metal Glenoid—Surgical Technique." 2008, 2009. <http://www.zimmer.com/content/pdf/en-US/Trabecular_Metal_Glenoid_Surgical_Technique_97-4301-204-00_Rev_1_11_2009_US_ONLY.pdf> Last Accessed: May 1, 2014.

"Assembly/Disassembly Instructions," Product: CMI Reamer, Tornier, Inc., available as early as Jan. 2013, pp. 1-2.

"Global Steptech Anchor Peg Glenoid Surgical Technique," DePuy Orthopaedics, Inc., Mar. 2014, pp. 1-32.

"Global Enable Glenoid Exposure Simplified—Design Rationale and Surgical Technique." DePuy Orthopaedics, Inc., 2010. pp. 1-24.

* cited by examiner

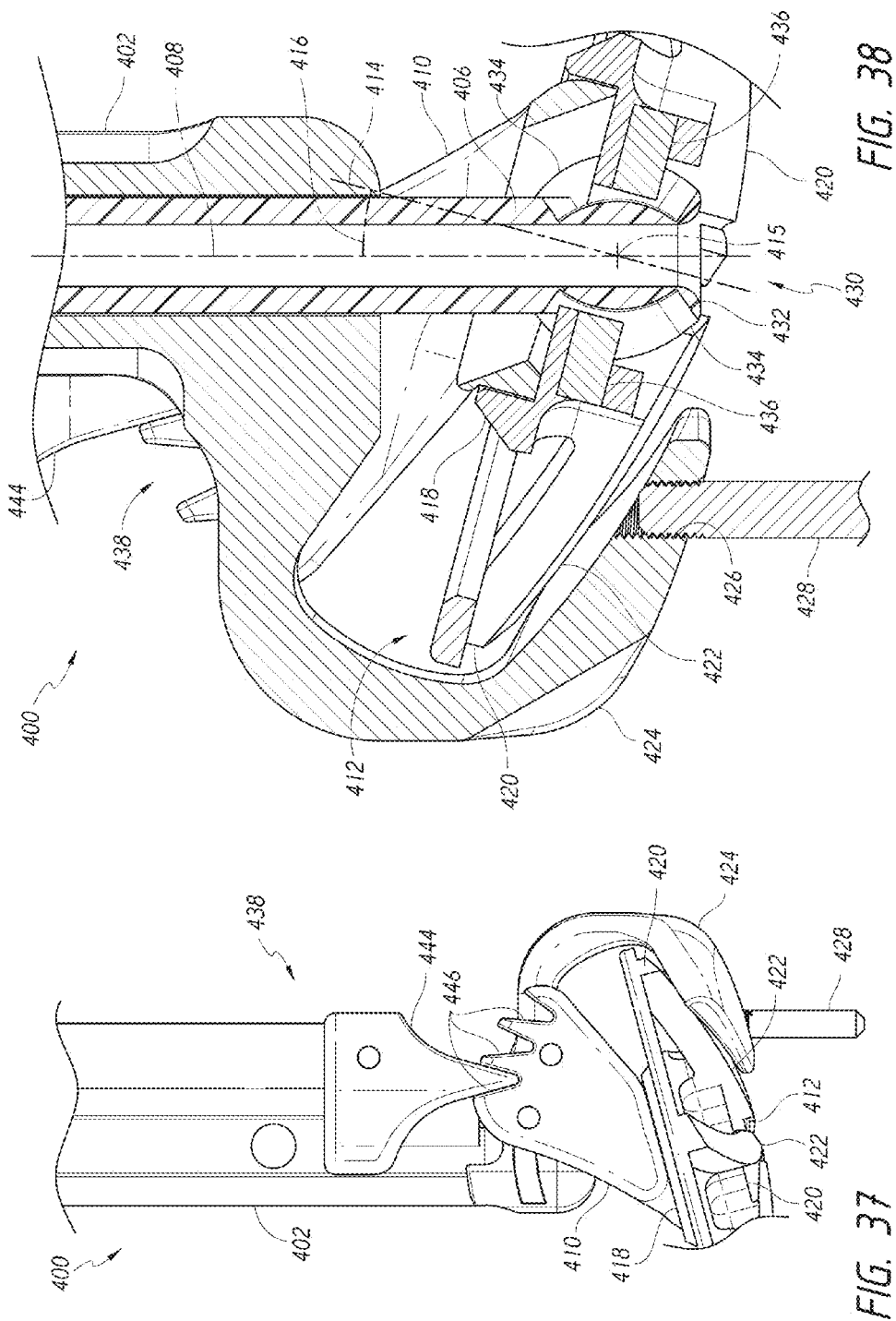

AUGMENTED GLENOID COMPONENTS AND DEVICES FOR IMPLANTING THE SAME

TECHNICAL FIELD

The present invention relates to glenoid implants and devices that facilitate implanting the same. In particular, the present invention relates to implants for glenoids having non-uniform erosion and devices that facilitate implanting the same.

BACKGROUND

In a healthy shoulder joint, the head of the humerus interacts with the glenoid of the scapula to form a "ball and socket" joint. The humeral head abuts and articulates with the glenoid to provide a wide range of motion. In an unhealthy shoulder joint, the interaction between the glenoid and the humerus is compromised, requiring repair or replacement.

In some unhealthy shoulder joints, different portions of the glenoid can experience different amounts of bone erosion. For example and referring to FIGS. 1-4, a glenoid 10 may include a posterior portion 12 that has a significant amount of erosion and an anterior portion 14 that has little or no erosion. Such a glenoid is commonly referred to as a "type-B2" glenoid. As another example, a glenoid may include a supero-posterior portion that has a significant amount of erosion and an infero-anterior portion that has little or no erosion. As yet another example, a glenoid may include an infero-posterior portion that has a significant amount of erosion and a supero-anterior portion that has little or no erosion. In any of these cases, a surgeon may need to remove a significant amount of bone, specifically, cortical bone of the relatively healthy portions of the glenoid, to accommodate typical glenoid implants.

Previously, glenoid components were developed that were specifically intended to be used with type-B2 glenoids and address the issues of typical glenoid components described above. Some of these glenoid components, for example, include a scapula-facing surface in which different portions of the surface are disposed at different "elevations". These components also include a transversely-extending surface that connects the different portions of the scapula-facing surface. These surfaces provide the glenoid component with a "stepped" appearance. However, these glenoid components nevertheless require a significant amount of bone removal and typically violate the subchondral plate. In addition, it is relatively difficult to remove bone to form an appropriately shaped surface for receiving a step-shaped glenoid component, and a surgeon must frequently insert a trial implant to check the fit with the surface.

FIGS. 5A-5C illustrate a glenoid 10 at different stages of traditional on-axis reaming. FIG. 5A illustrates a glenoid 10 with a portion of bone 11 that has deteriorated from the posterior portion 12. FIG. 5B illustrates a reamer 15 approaching the glenoid 10 along a longitudinal axis L of the glenoid 10. Portion 13 indicates the portion of bone to be removed using the reamer 15. As shown in FIG. 5C, following on-axis reaming, a significant portion 13 of the glenoid 10 has been unnecessarily removed from both the posterior portion 12 and the anterior portion 14.

As another example, FIGS. 6A-6C illustrate a glenoid 10 following off-axis reaming at different angles. Traditionally, to accomplish off-axis reaming, the entire reamer 15 is introduced into the body at an angle (i.e., 8 degrees, 12 degrees, or 18 degrees) relative to the longitudinal axis L of the bone. However, as shown in FIGS. 6A-6C, a greater portion of the anterior portion 14 is still unnecessarily removed from the glenoid 10 than is necessary for the implantation of glenoid components created for type-B2 glenoids.

FIGS. 7A and 7B illustrate yet another glenoid 10 following preparation of the bone for the insertion of a GLOBAL® STEPTECH® Anchor Peg Glenoid. In this method, a significant portion of the posterior portion 12 of the glenoid 10 has been unnecessarily removed in a stepped manner. Accordingly, there is a need for a device that minimizes the amount of bone removed.

Others of these glenoid components, for example, include a scapula-facing surface that has a constant slope. However, forces acting on the proximal or articulation surface of these components urge the sloped scapula-facing surface to slide over the prepared glenoid. This action, in turn, applies shear forces to posts or anchors that extend from the scapula-facing surface and couple to the bone. These glenoid components also present challenges to surgeons. Specifically, the reaming path for preparing the glenoid is typically across the glenoid.

SUMMARY

In some embodiments, a glenoid component for coupling to a scapula of a subject includes a body. The body includes an articulation surface adapted to articulate with a humeral component, and the body further includes a distal surface adapted to face the glenoid of the scapula. The distal surface includes a base surface portion including a first convex surface adapted to face a first portion of the glenoid. The distal surface further includes an augmented surface portion including a second convex surface adapted to face a second portion of the glenoid. The base surface portion and the augmented surface portion are connected therebetween by an interface. The first convex surface may include a first radius of curvature and the second convex surface may include a second radius of curvature. In particular embodiments, the first and second radius of curvature may be the same. The first convex surface may extend from the interface to an anterior portion of the glenoid implant. The second convex surface may extend from the interface to at least one of a posterior portion, supero-posterior portion or an infero-posterior portion of the implant.

In some embodiments, a device for removing bone from a glenoid of a subject includes a frame that is adapted to be manipulated by a user. A drive shaft is rotatably supported by the frame and adapted to be rotatably driven about a drive axis. A reaming head includes at least one reaming edge adapted to engage the glenoid of the subject. The reaming head is adapted to be rotatably driven about a reaming axis by the drive shaft, and the reaming axis is non-parallel to the drive axis.

In some embodiments, a device for removing bone from a glenoid of a subject includes a frame adapted to be manipulated by a user and a reaming head including a reaming surface. A drive shaft is rotatably supported by and extends through the frame and has a distal end coupled with the reaming head. The drive shaft is adapted to be rotatably driven about a drive shaft axis. A guard member is coupled to a distal portion of the frame. The guard member is configured to inhibit a portion of the reaming surface from engaging bone.

In some embodiments, a device for removing bone from a glenoid of a subject includes a frame adapted to be manipulated by a user and a reaming head including a reaming surface. A cannulated drive shaft is rotatably supported by and extends at least partially through the frame and has a distal end coupled with the reaming head. The drive shaft is adapted to be rotatably driven about a drive shaft axis. The device has a first configuration to rotate the reaming head about a first reaming axis when the reaming head is in a first orientation. The device has a second configuration to rotate the reaming head about a second reaming axis when the reaming head is in a second orientation.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

BRIEF DESCRIPTION OF THE DRAWINGS

FIG. 37 is a detail front view of a distal end of the reaming device of FIG. 32.

FIG. 38 is a detail rear longitudinal sectional view of the distal end of the reaming device of FIG. 32. A reaming head of the reaming device is shown in a first orientation.

Figure 3:
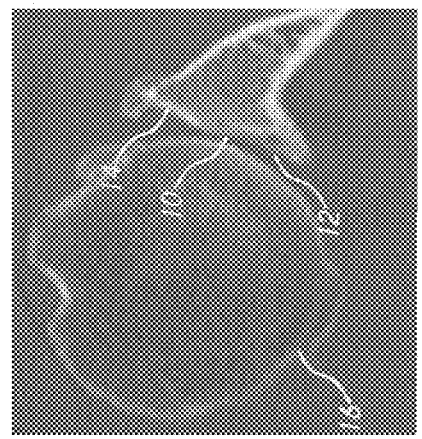
FIGS. 1-4 are illustrations of type-B2 glenoids.
Figure 2:
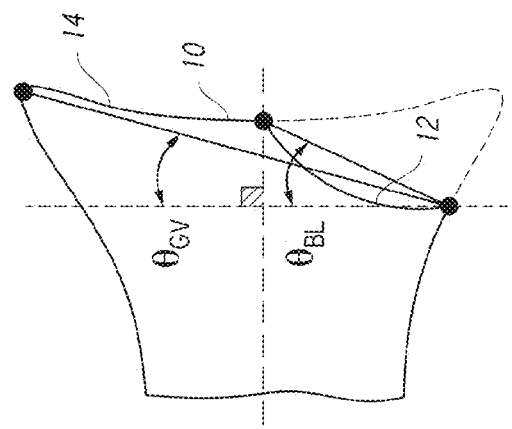

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

Figure 1:
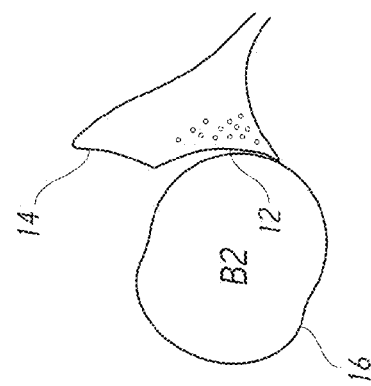
Figure 4:
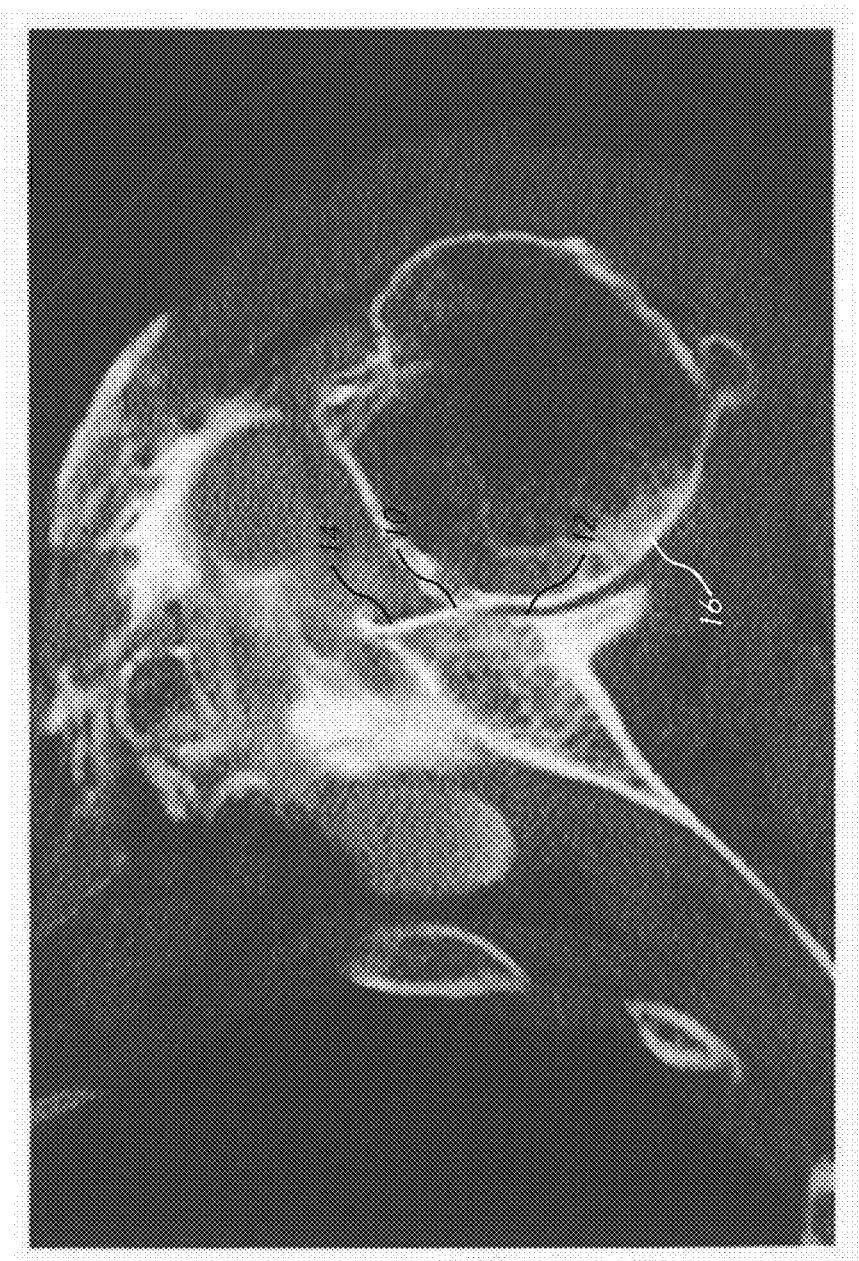
Figure 5A:
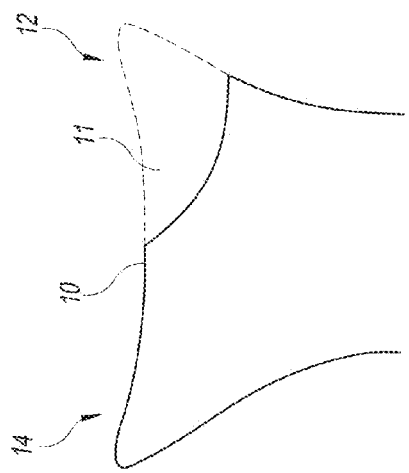
FIGS. 5A-5C illustrate a glenoid at different stages of a traditional method of on-axis reaming.
Figure 5B:
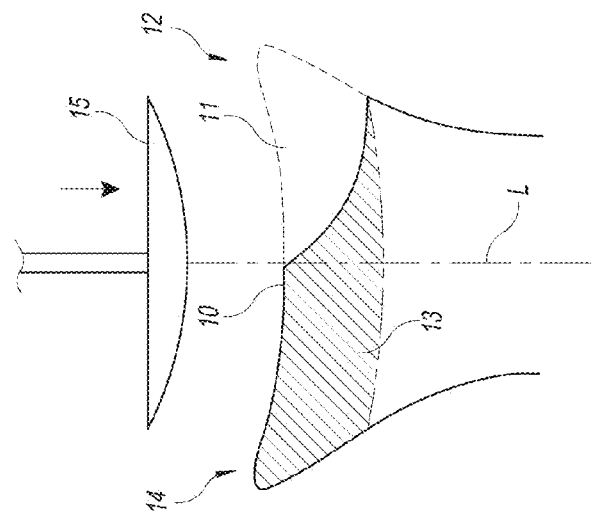
Figure 5C:
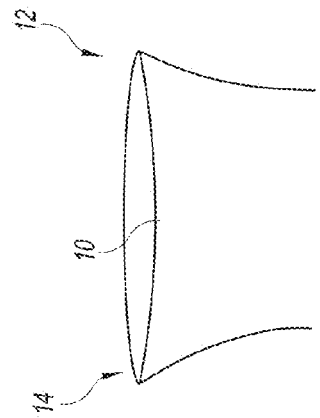
Figure 6C:
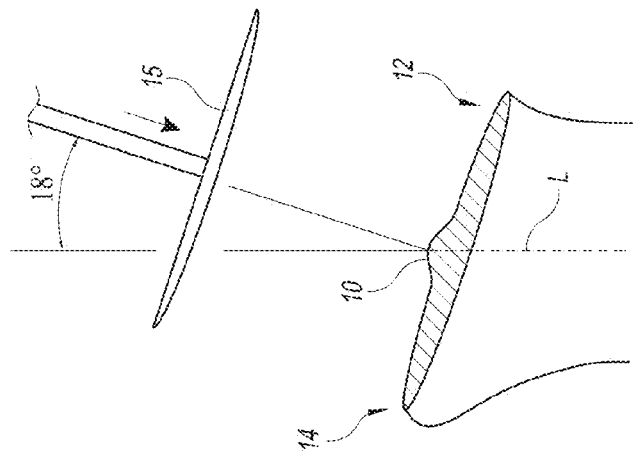
FIGS. 6A-6C illustrate glenoids following traditional off-axis reaming at different angles.
Figure 6B:
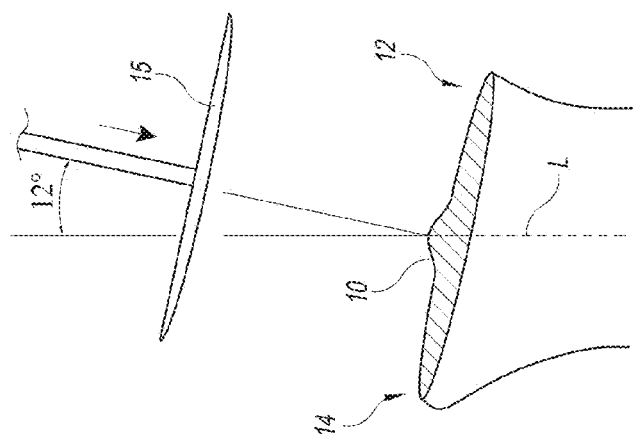
Figure 6A:
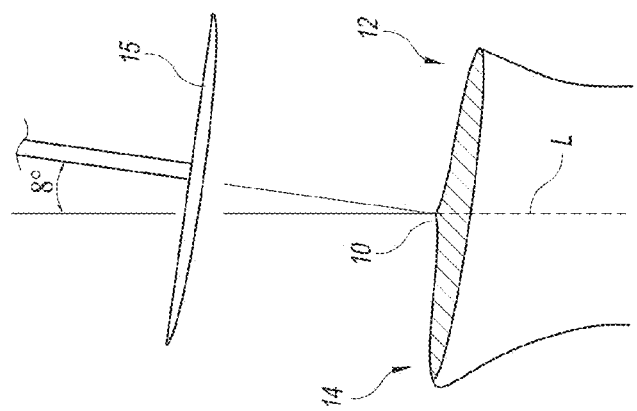
Figure 7B:
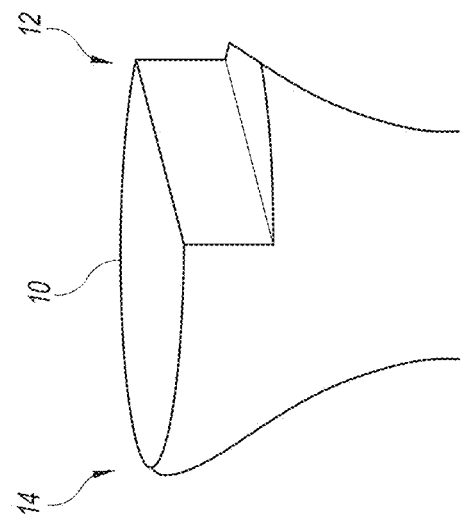
FIGS. 7A and 7B illustrate a glenoid at different stages of a method of reaming in preparation for the GLOBAL® STEPTECH® Anchor Peg Glenoid.
Figure 7A:
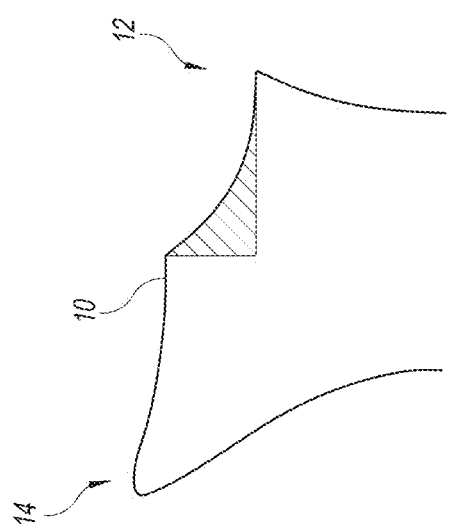
Figure 8:
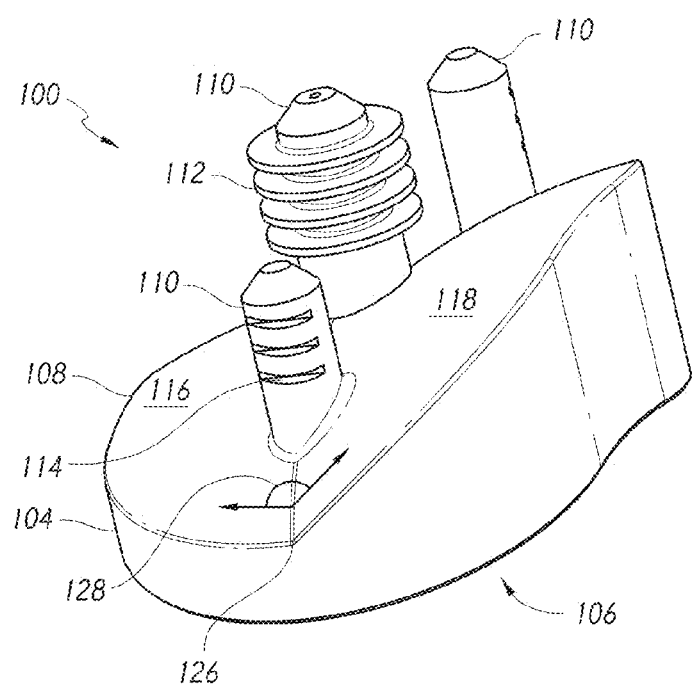
FIG. 8 is a perspective view of a glenoid component according to embodiments of the present invention.
Figure 9:
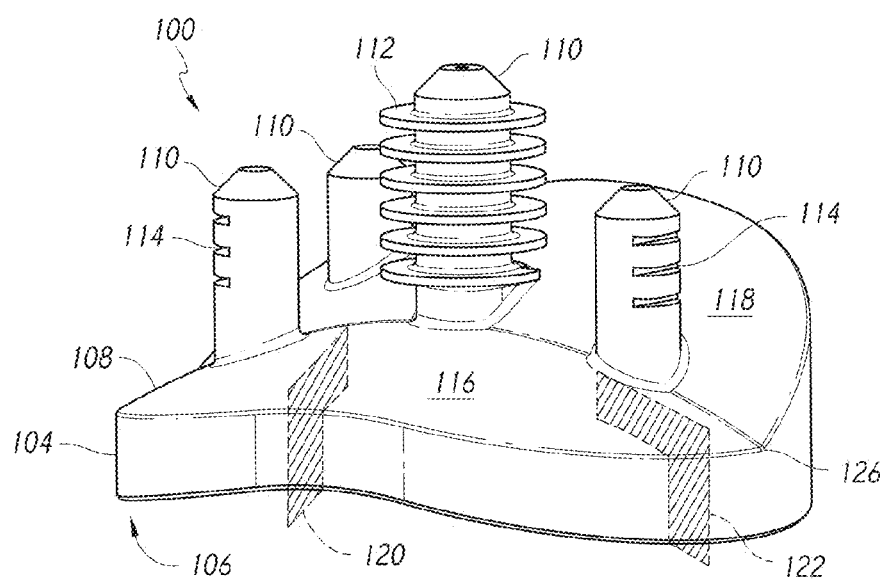
FIG. 9 is another perspective view of the glenoid component of FIG. 8.
Figure 10:
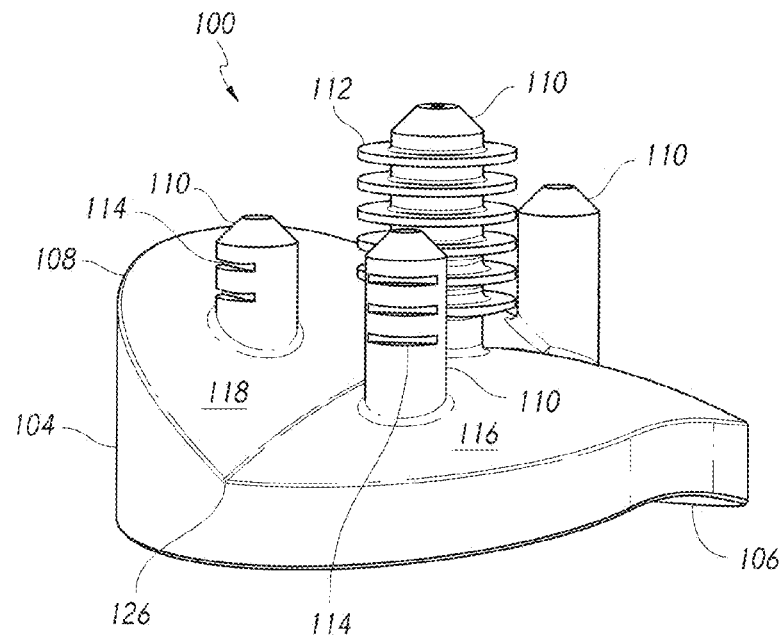
FIG. 10 is another perspective view of the glenoid component of FIG. 8.
Figure 11:
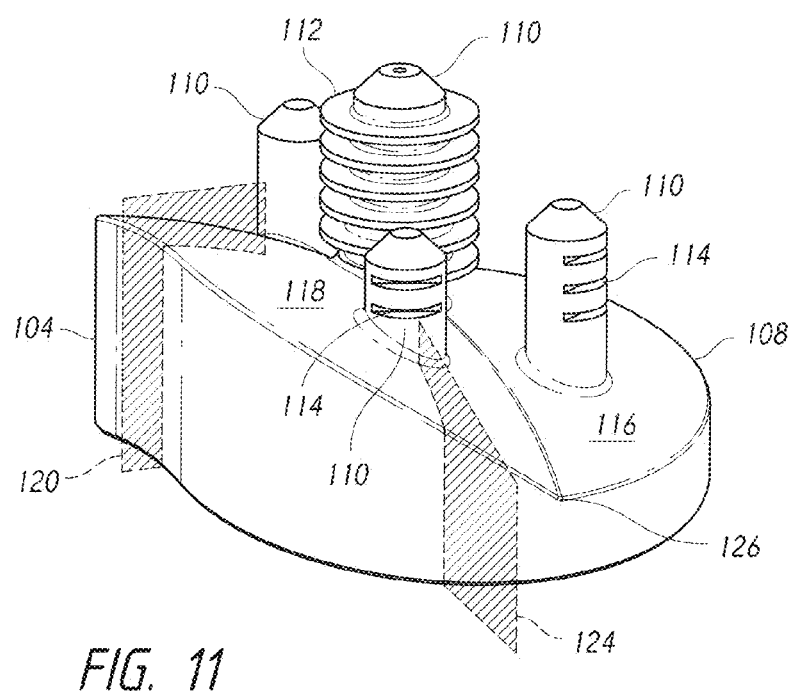
FIG. 11 is another perspective view of the glenoid component of FIG. 8.
Figure 12:
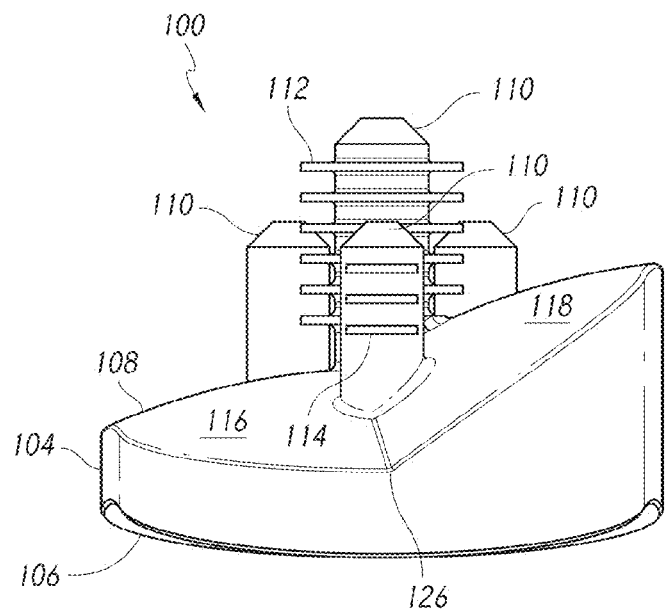
FIG. 12 is a top view of the glenoid component of FIG. 8.
Figure 13:
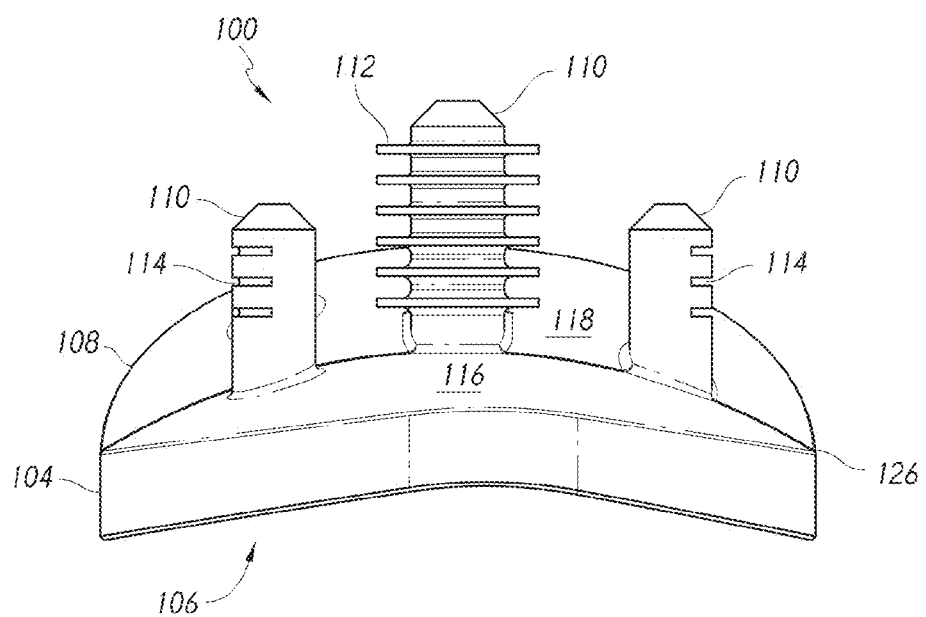
FIG. 13 is a side view of the glenoid component of FIG. 8.
Figure 14:
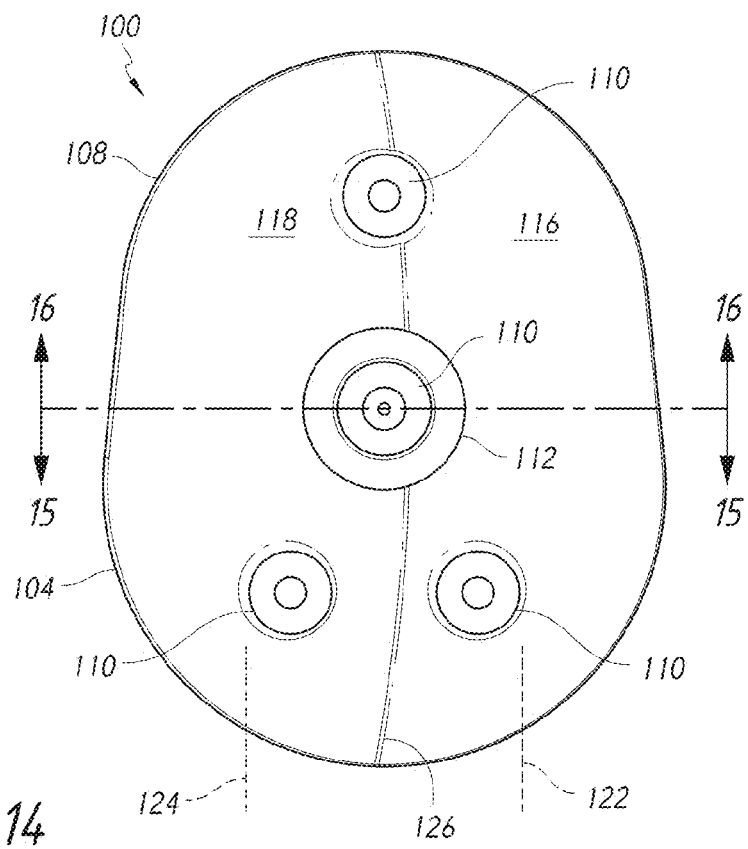
FIG. 14 is a front view of the glenoid component of FIG. 8.

FIGS. 8-17 illustrate an exemplary glenoid component or implant 100 according to embodiments of the present invention. The glenoid component 100 is adapted to be positioned between the scapula of a subject (not shown) and a humeral component. The glenoid component 100 is also adapted to articulate with the humeral component. The humeral component may be a humeral prosthesis secured to the humerus of the subject or an anatomical humeral head of the subject (see, for example, the humeral head 16 shown in FIG. 1).

The glenoid component 100 includes a body 104 having a proximal or articulation surface 106. The articulation surface 106 is concave and adapted to engage the humeral component. The articulation surface 106 receives at least a portion of the humeral component within the concavity defined by the articulation surface 106.

Opposite the articulation surface 106, the body 104 includes a distal or scapula-facing surface 108. In some embodiments, the distal surface 108 supports one or more securing and/or stabilizing anchors, pins, or posts 110 (referred to herein as anchors). The anchors 110 may be received in pre-drilled holes in the scapula (not shown). The anchors 110 may have generally cylindrical shapes, and the ends opposite the body 104 of the glenoid component 100 may be conical or frusto-conical to facilitate insertion into the pre-drilled holes formed in the scapula. The anchors 110 may have various lengths and/or different lengths relative to each other.

The anchors 110 may have features that facilitate securement to the scapula. For example, one or more of the anchors 110 may include one or more radially-outwardly extending fins 112. As another example, one or more of the anchors 110 may include one or more transversely extending grooves 114.

The anchors 110 may be arranged on the distal surface 108 in various manners. For example and as shown in the figures, one anchor 110 may be centrally positioned, one anchor 110 may be superiorly positioned, and two anchors 110 may be inferiorly positioned.

In some embodiments, the anchors 110 may be arranged and configured in any of the manners described in U.S. Patent App. Pub. 2010/0228352, published on Sep. 9, 2010, which is hereby incorporated by reference in its entirety. In other embodiments one or more anchors may include a keel, finned keel, or other structures. See for example U.S. Patent App. Pub. 2013/0144393, published on Jun. 6, 2013, which is hereby incorporated by reference in its entirety.

The distal surface 108 of the glenoid component 100 is adapted to face the glenoid of the subject. In some embodiments, the glenoid may be an anatomical type-B2 glenoid (see, for example, the glenoid 10 shown in FIG. 1) or a type-B2 glenoid that is at least partially prepared for receiving the glenoid component 100 (for example, by removing bone from the glenoid).

The distal surface 108 of the glenoid component 100 includes different portions that face different portions of the glenoid. The different portions of the glenoid may have experienced different amounts of bone erosion. Specifically, the distal surface 108 includes a base surface portion 116 that is adapted to face a first portion of the glenoid. In some embodiments, the first portion is a relatively healthy (that is, having little or no bone erosion) anterior portion of the glenoid. The anterior portion of the glenoid may be an anatomical surface or a surface that is at least partially prepared for receiving the glenoid component 100. The distal surface 108 also includes an augmented surface portion 118 that is adapted to face a second portion of the glenoid. In some embodiments, the second portion is a relatively unhealthy (that is, having a significant amount of bone erosion) posterior portion of the glenoid. The posterior portion of the glenoid may be an anatomical surface or a surface that is at least partially prepared for receiving the glenoid component 100.

Figure 15:
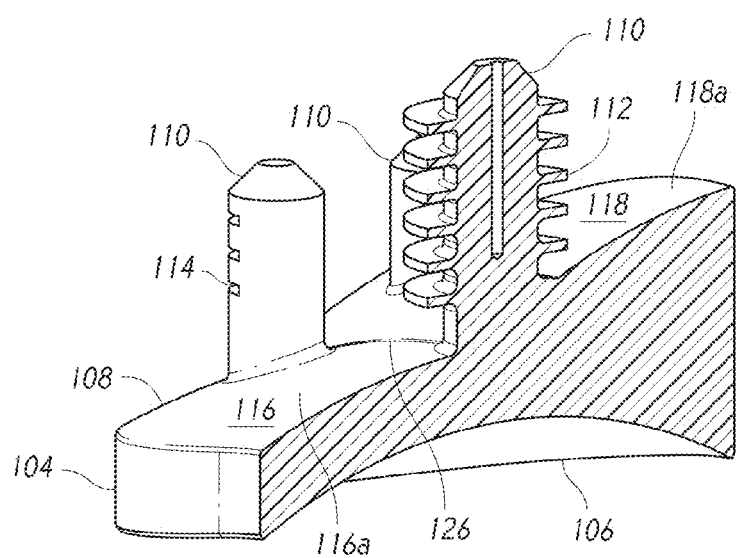
FIG. 15 is a perspective sectional view of the glenoid component along line 15-15 of FIG. 14.
Figure 16:
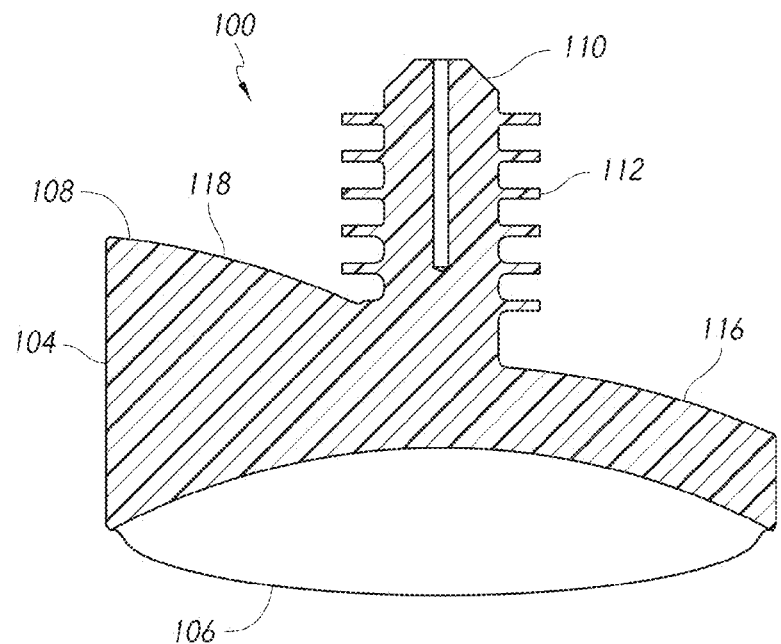
FIG. 16 is a bottom sectional view of the glenoid component along line 16-16 of FIG. 14.
Figure 17:
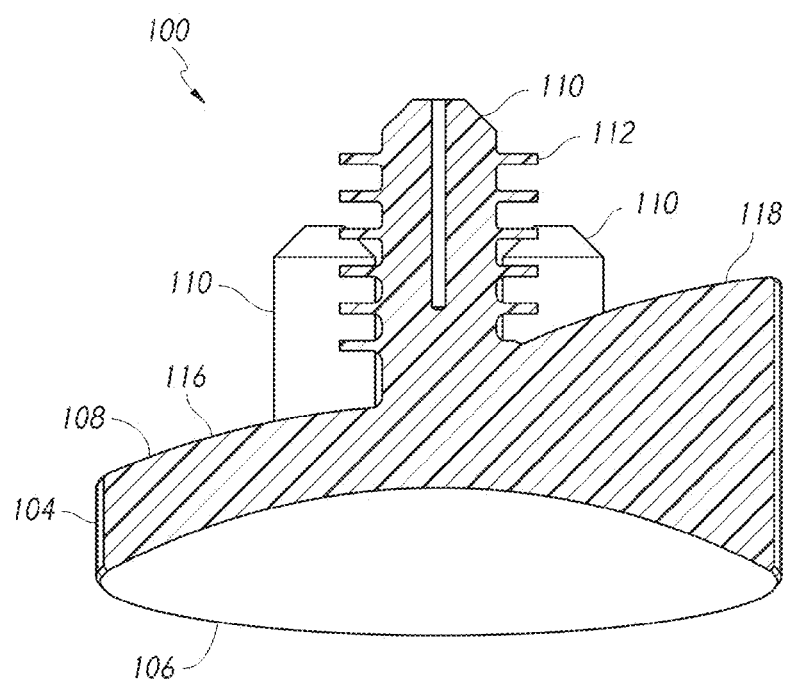
FIG. 17 is a top sectional view of the glenoid component along line 15-15 of FIG. 14.
Figure 18:
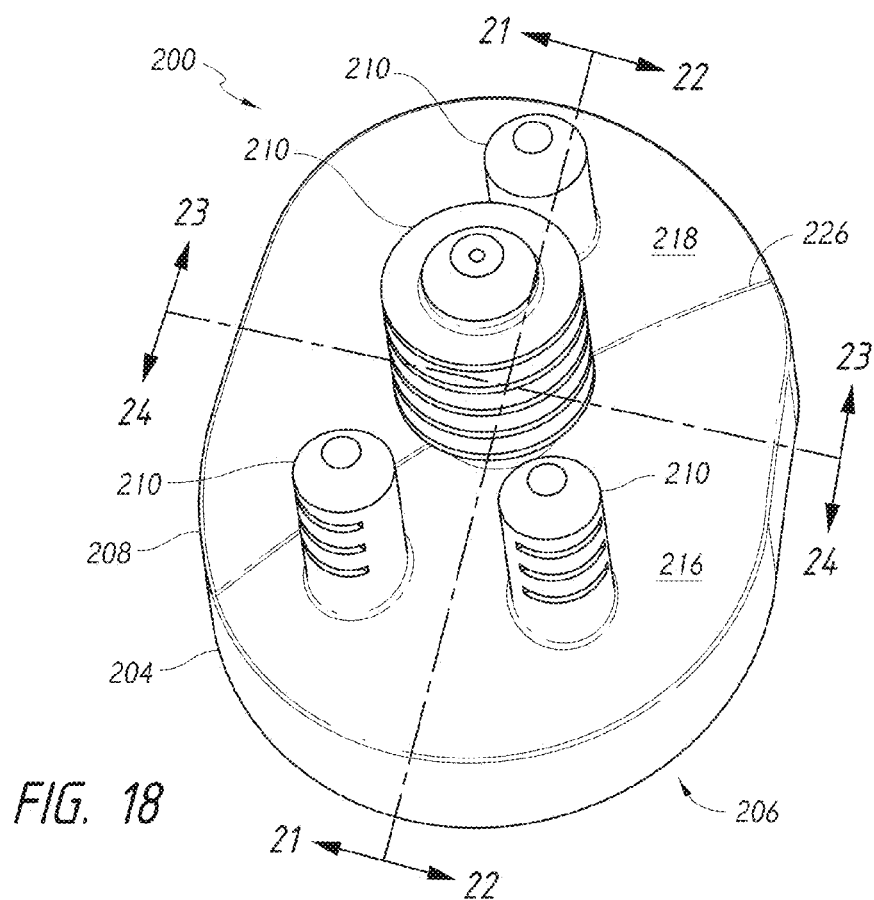
FIG. 18 is a perspective view of a glenoid component according to embodiments of the present invention.
Figure 19:
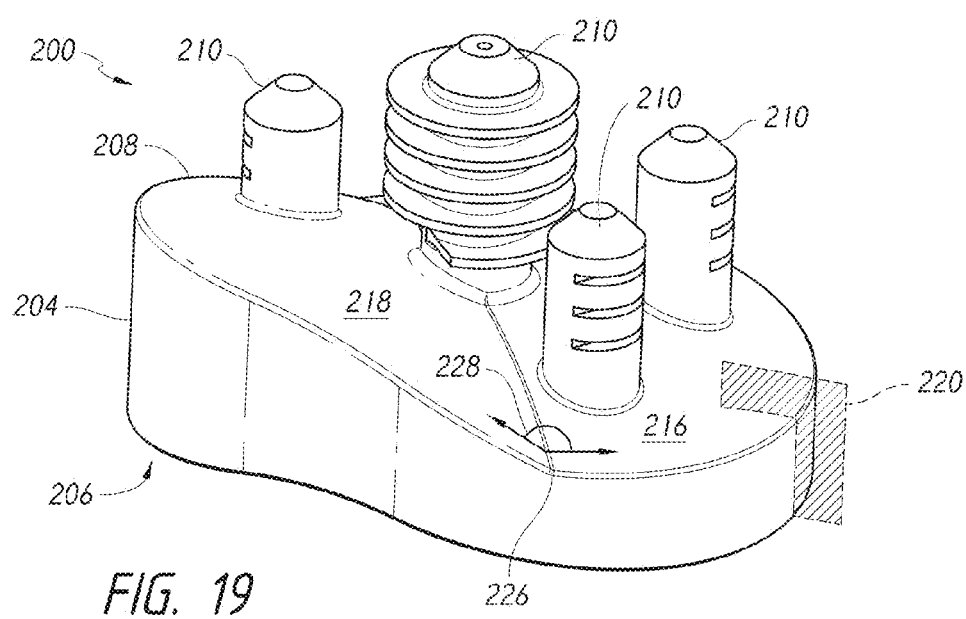
FIG. 19 is another perspective view of the glenoid component of FIG. 18.
Figure 20:
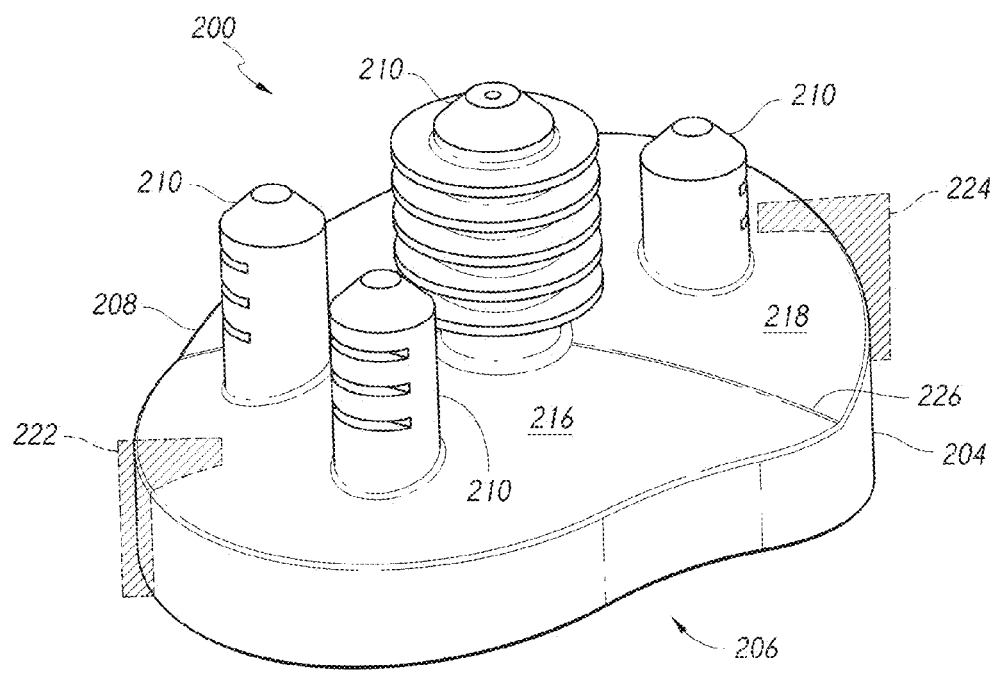
FIG. 20 is another perspective view of the glenoid component of FIG. 18.
Figure 21:
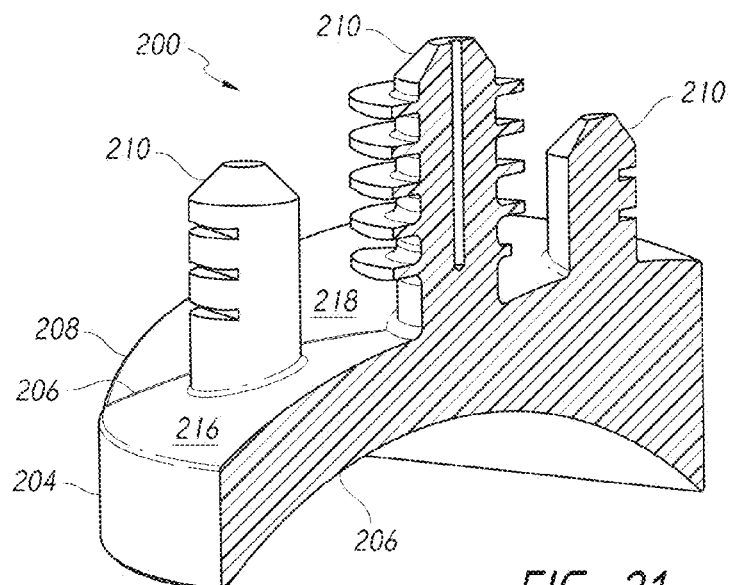
FIG. 21 is a perspective section view of the glenoid component along line 21-21 of FIG. 18.
Figure 22:
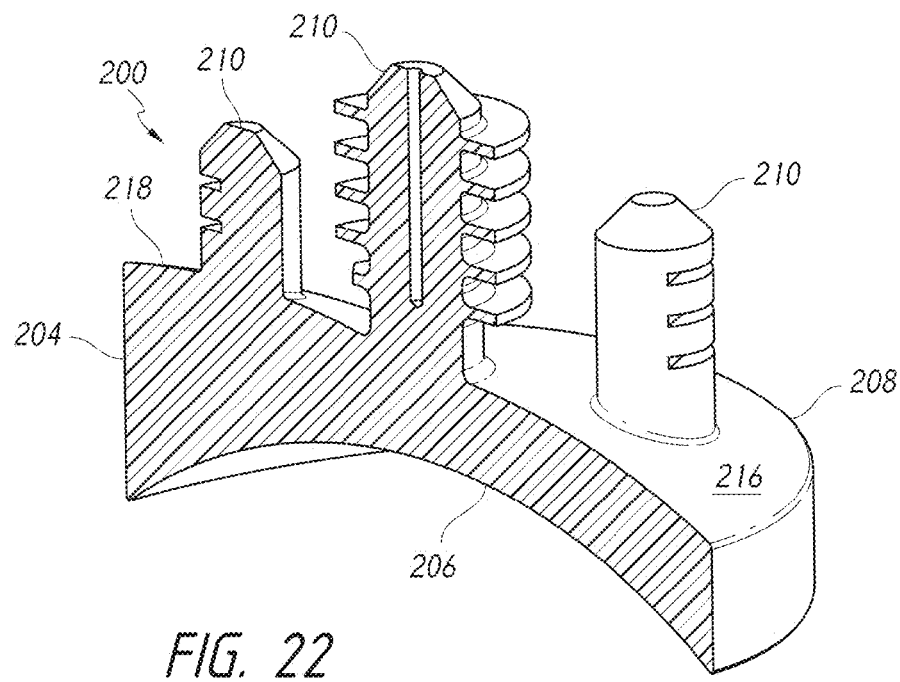
FIG. 22 is a perspective sectional view of the glenoid component along line 22-22 of FIG. 18.
Figure 23:
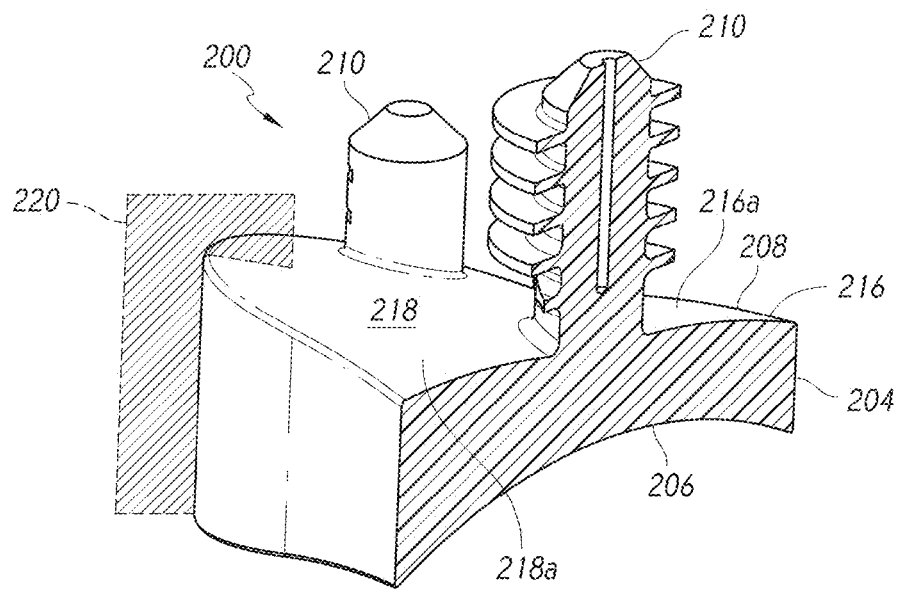
FIG. 23 is a perspective sectional view of the glenoid component along line 23-23 of FIG. 18.
Figure 24:
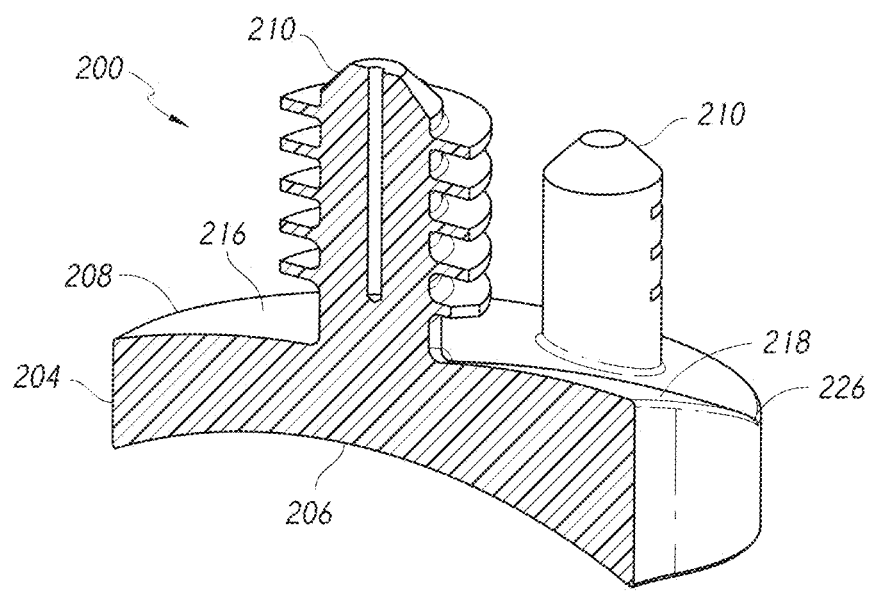
FIG. 24 is a perspective sectional view of the glenoid component along line 24-24 of FIG. 18.
Figure 25:
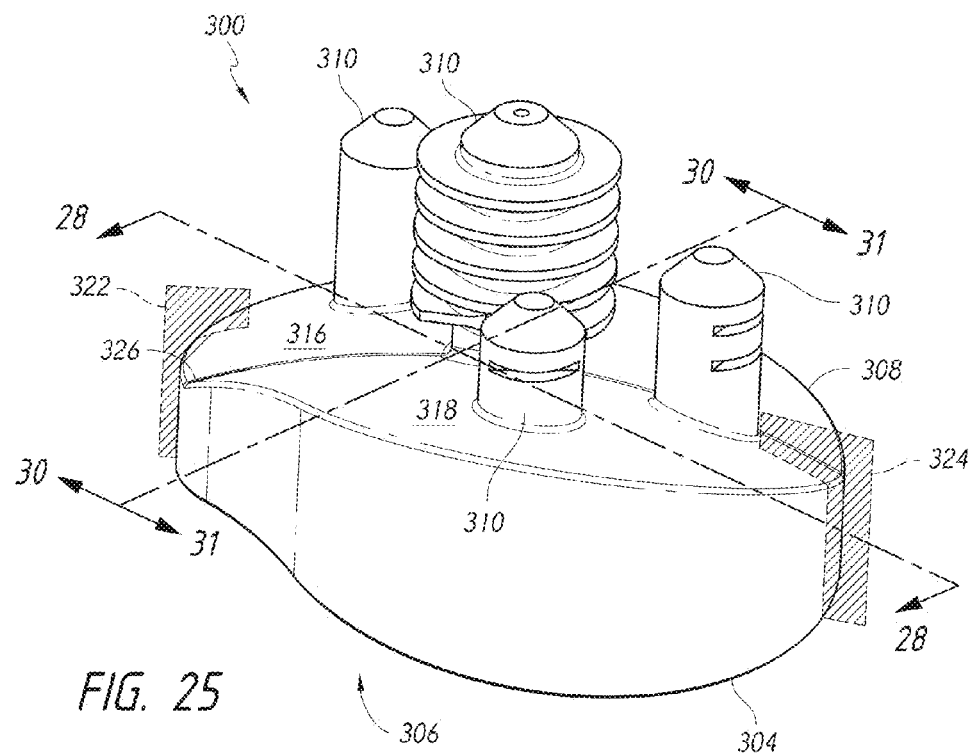
FIG. 25 is a perspective view of a glenoid component according to embodiments of the present invention.
Figure 26:
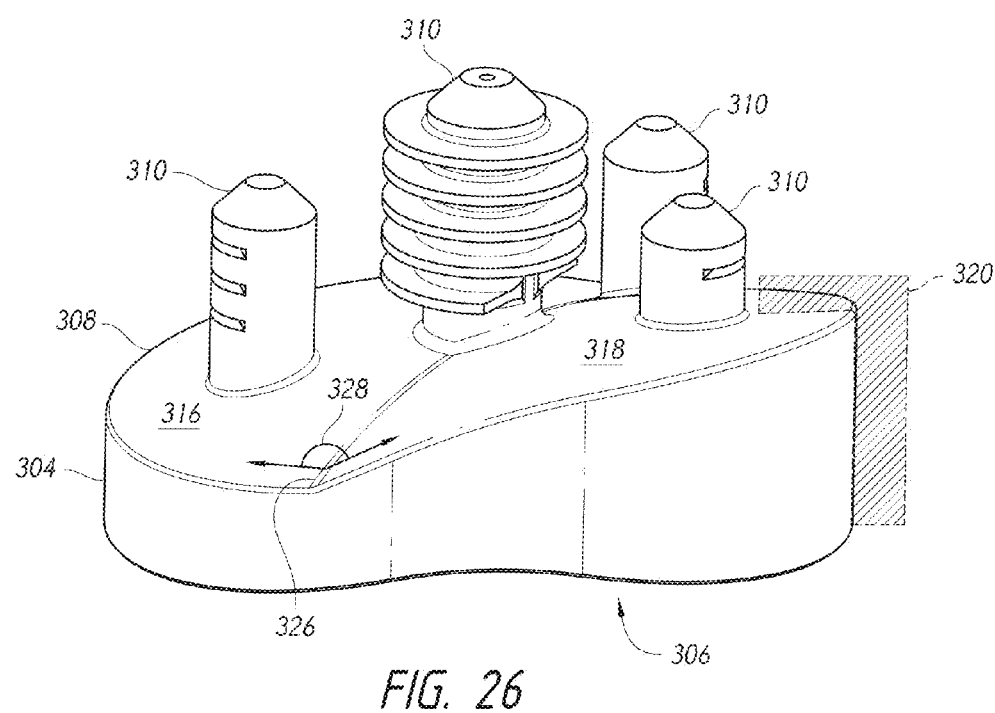
FIG. 26 is another perspective view of the glenoid component of FIG. 25.
Figure 27:
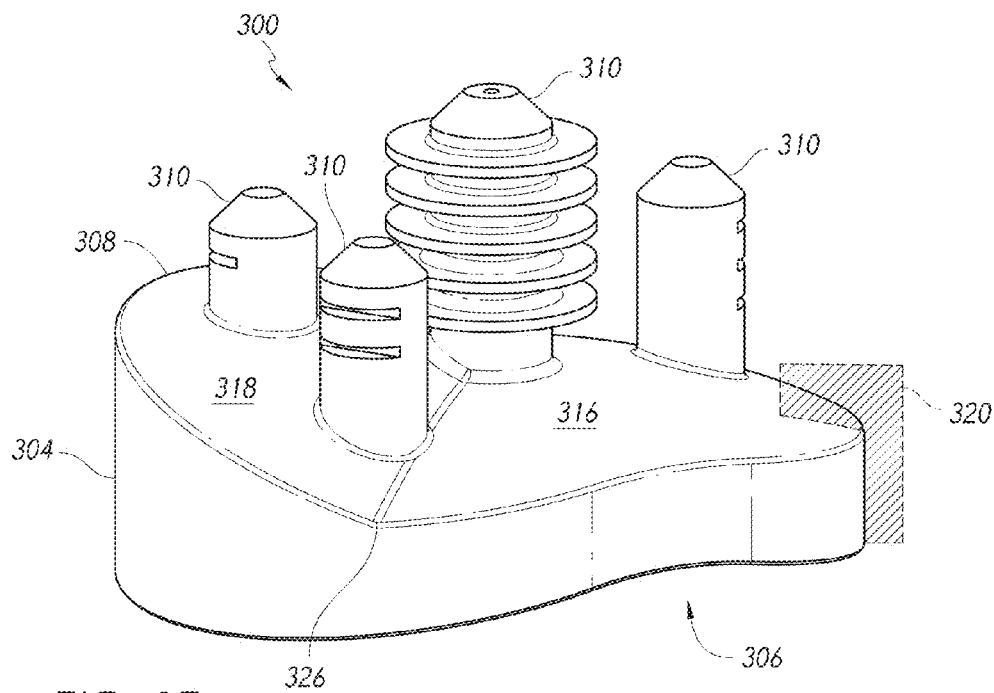
FIG. 27 is another perspective view of the glenoid component of FIG. 25.
Figure 28:
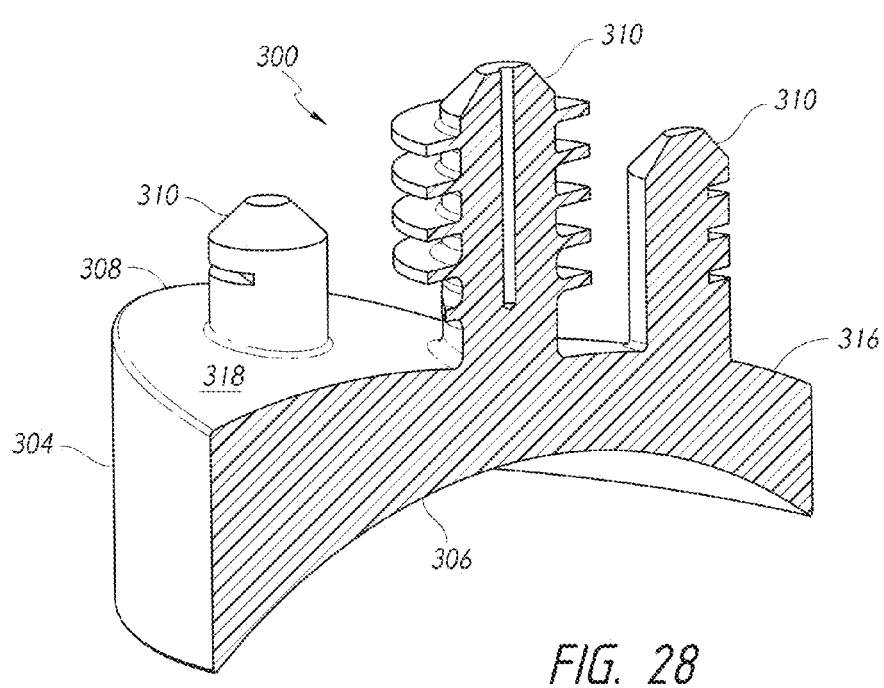
FIG. 28 is a perspective section view of the glenoid component along line 28-28 of FIG. 25.
Figure 29:
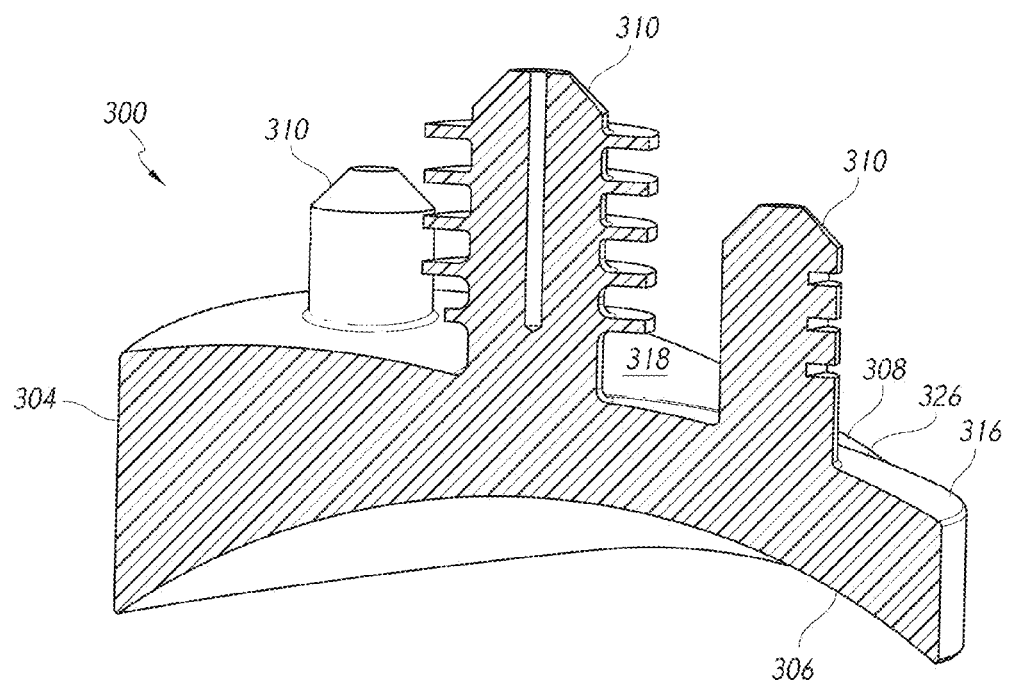
FIG. 29 is another perspective sectional view of the glenoid component along line 28-28 of FIG. 25.
Figure 30:
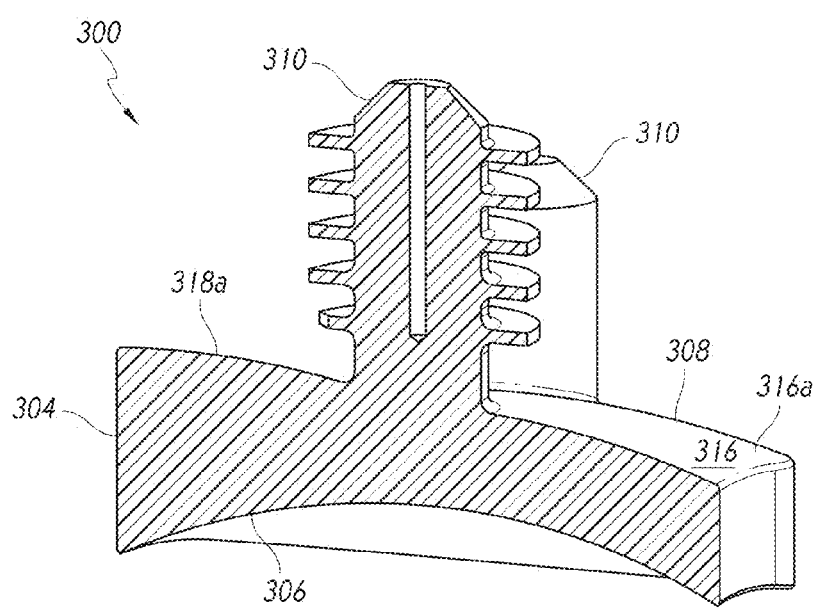
FIG. 30 is a perspective sectional view of the glenoid component along line 30-30 of FIG. 25.
Figure 31:
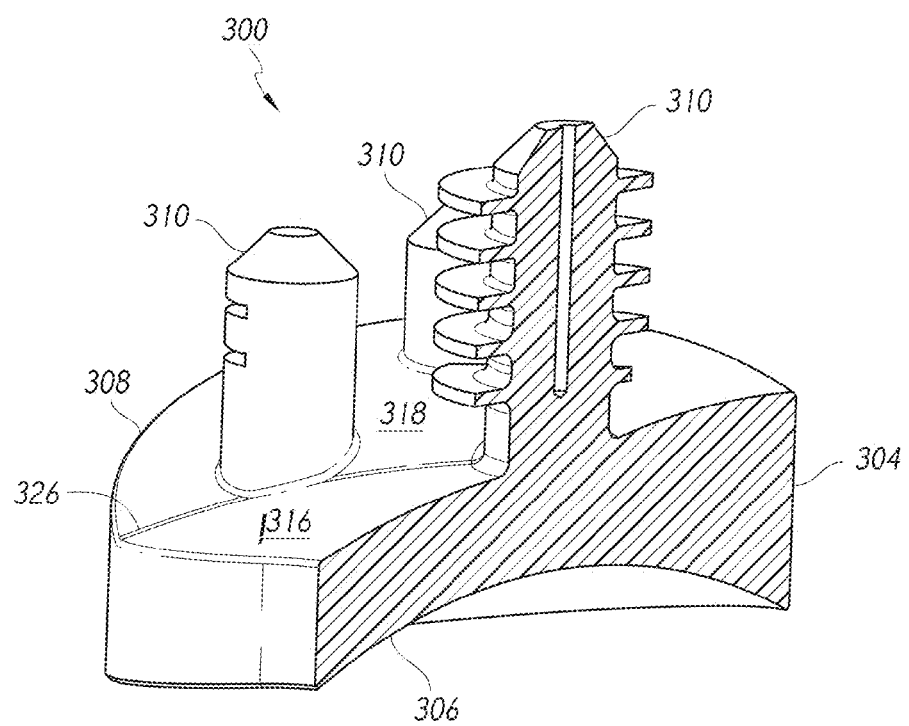
FIG. 31 is a perspective sectional view of the glenoid component along line 31-31 of FIG. 25.
Figure 32:
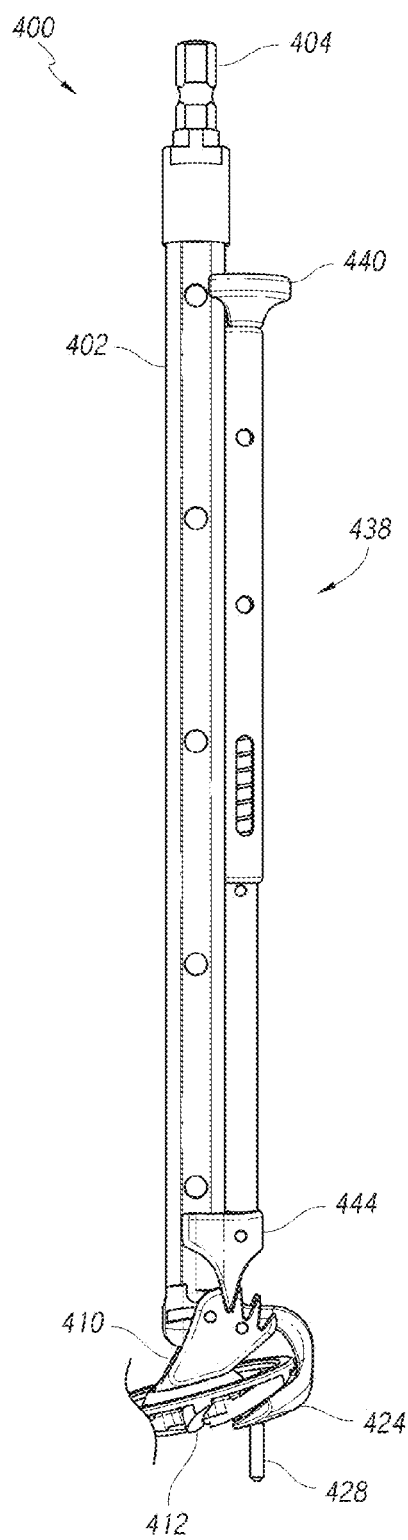
FIG. 32 is a front view of a reaming device according to embodiments of the present invention.

As shown most clearly in FIGS. 15-17, the augmented surface portion 118 is generally disposed further from the articulation surface 106 than the base surface portion 116. Stated another way, the body 104 of the glenoid component 100 is relatively thin between base surface portion 116 and the articulation surface 106. In contrast, the body 104 of the glenoid component 100 is relatively thick between the augmented surface portion 118 and the articulation surface 106.

In some embodiments, the base surface portion 116 is a convex surface. The base surface portion 116 may have a curved shape (for example, an arcuate shape) in a transverse plane 120 that extends through the articulation surface 106, the base surface portion 116, and the augmented surface portion 118 (that is, a plane extending through the body 104 in a thickness direction and substantially bisecting each of the surfaces 106, 116, and 118; see FIG. 9). The base surface portion 116 may have a curved shape (for example, an arcuate shape) in a longitudinal plane 122 that extends through the articulation surface 106 and the base surface portion 116 and is disposed apart from the augmented surface portion 118 (that is, a plane extending through the body 104 in a thickness direction, substantially perpendicular to the transverse plane 120, substantially bisecting the base surface portion 116, and not intersecting with the augmented surface portion 118; see FIG. 9).

In some embodiments, the augmented surface portion 118 is a convex surface. The augmented surface portion 118 may have a curved shape (for example, an arcuate shape) in the transverse plane 120 (see FIG. 11). The augmented surface portion 118 may have a curved shape (for example, an arcuate shape) in a longitudinal plane 124 that extends through the articulation surface 106 and the augmented surface portion 118 and is disposed apart from the base surface portion 116 (that is, a plane extending through the body 104 in a thickness direction, substantially parallel to the longitudinal plane 122, substantially bisecting the augmented surface portion 118, and not intersecting with the base surface portion 116; see FIG. 11).

The augmented surface portion 118 and the base surface portion 116 intersect at an interface 126. In other words, the base surface portion 116 and the augmented surface portion 118 are connected by or intersect at the interface 126. In some embodiments, the augmented surface portion 118 and the base surface portion 116 define an obtuse angle 128 at the interface 126 (see FIG. 8). More specifically, the base surface portion 116 has a first convex surface 116a, extending from the interface 126 to an anterior portion of the implant and adapted to face a first portion of the glenoid. The augmented surface portion 118 has a second convex surface 118a, extending from the interface to at least one of a posterior portion, a supero-posterior portion, or an infero portion of the glenoid implant and adapted to face a second portion of the glenoid. Stated another way, the base surface portion 116 has a first, relatively-gradual slope toward the interface 126 and the augmented surface portion 118 has a second, relatively-inclined slope toward the interface 126. The first convex surface 116a has a first radius of curvature and the second convex surface 118a has a second radius of curvature. The first radius of curvature and the second radius of curvature may be the same or different. In some embodiments, the interface 126 substantially extends in a direction parallel to the longitudinal planes 122 and 124 (see FIG. 14). That is, the interface 126 may curve slightly relative to the planes 122 and 124 due to the shapes of the augmented surface portion 118 and the base surface portion 116.

FIGS. 18-24 illustrate an exemplary glenoid component or implant 200 according to embodiments of the present invention. The glenoid component 200 is adapted to be positioned between the scapula of a subject and a humeral component. The glenoid component 200 is also adapted to articulate with the humeral component. The humeral component may be a humeral prosthesis secured to the humerus of the subject or an anatomical humeral head of the subject (see, for example, the humeral head 16 shown in FIG. 1).

The glenoid component 200 includes a body 204 having a proximal or articulation surface 206. The articulation surface 206 is concave and adapted to engage the humeral component. The articulation surface 206 receives at least a portion of the humeral component within the concavity defined by the articulation surface 206.

Opposite the articulation surface 206, the body 204 includes a distal or scapula-facing surface 208. In some embodiments, the distal surface 208 supports one or more securing and/or stabilizing anchors, pins, or posts 210 which may have the same features and/or be arranged in the same manner as the anchors 110 described above.

The distal surface 208 of the glenoid component 200 is adapted to face the glenoid of the subject. In some embodiments, the glenoid may be an anatomical glenoid that has significant supero-posterior erosion and little or no infero-anterior erosion or such a glenoid that is at least partially prepared for receiving the glenoid component 200 (for example, by removing bone from the glenoid).

The distal surface 208 of the glenoid component 200 includes different portions that face different portions of the glenoid. Specifically, the distal surface 208 includes a base surface portion 216 that is adapted to face the infero-anterior portion of the glenoid. The distal surface 208 also includes an augmented surface portion 218 that is adapted to face the supero-posterior portion of the glenoid.

As shown most clearly in FIGS. 21-24, the augmented surface portion 218 is generally disposed further from the articulation surface 206 than the base surface portion 216. Stated another way, the body 204 of the glenoid component 200 is relatively thin between base surface portion 216 and the articulation surface 206. In contrast, the body 204 of the glenoid component 200 is relatively thick between the augmented surface portion 218 and the articulation surface 206.

In some embodiments, the base surface portion 216 is a convex surface. The base surface portion 216 may have a curved shape (for example, an arcuate shape) in a plane 220 that extends through the articulation surface 206, the base surface portion 216, and the augmented surface portion 218 (that is, a plane extending through the body 204 in a thickness direction and substantially bisecting each of the surfaces 206, 216, and 218; see FIG. 19). The base surface portion 216 may have a curved shape (for example, an arcuate shape) in a plane 222 that extends through the articulation surface 206 and the base surface portion 216 and is disposed apart from the augmented surface portion 218 (that is, a plane extending through the body 204 in a thickness direction, substantially bisecting the base surface portion 216, and not intersecting with the augmented surface portion 218; see FIG. 20).

In some embodiments, the augmented surface portion 218 is a convex surface. The augmented surface portion 218 may have a curved shape (for example, an arcuate shape) in the plane 220 (see FIG. 23). The augmented surface portion 218 may have a curved shape (for example, an arcuate shape) in a longitudinal plane 224 that extends through the articulation surface 206 and the augmented surface portion 218 and is disposed apart from the base surface portion 216 (that is, a plane extending through the body 204 in a thickness direction, substantially bisecting the augmented surface portion 218, and not intersecting with the base surface portion 216; see FIG. 20).

The augmented surface portion 218 and the base surface portion 216 intersect at an interface 226. In other words, the base surface portion 216 and the augmented surface portion 218 are connected by or intersect at interface 226. In some embodiments, the augmented surface portion 218 and the base surface portion 216 define an obtuse angle 228 at the interface 226 (see FIG. 19). More specifically, the base surface portion 216 has a first convex surface 216a, extending from the interface 226 to an anterior portion of the implant and adapted to face a first portion of the glenoid. The augmented surface portion 218 has a second convex surface 218a, extending from the interface 226 to at least one of a posterior portion, a supero-posterior portion, or an infero portion of the glenoid implant and adapted to face a second portion of the glenoid. Stated another way, the base surface portion 216 has a first, relatively-gradual slope toward the interface 226 and the augmented surface portion 218 has a second, relatively-inclined slope toward the interface 226. The first convex surface 216a has a first radius of curvature and the second convex surface 218a has a second radius of curvature. The first radius of curvature and the second radius of curvature may be the same or different. In some embodiments, the interface 226 substantially extends in a direction parallel to the planes 222 and 224 (see FIG. 20). That is, the interface 226 may curve slightly relative to the planes 222 and 224 due to the shapes of the augmented surface portion 218 and the base surface portion 216.

FIGS. 25-31 illustrate an exemplary glenoid component or implant 300 according to embodiments of the present invention. The glenoid component 300 is adapted to be positioned between the scapula of a subject and a humeral component. The glenoid component 300 is also adapted to articulate with the humeral component. The humeral component may be a humeral prosthesis secured to the humerus of the subject or an anatomical humeral head of the subject (see, for example, the humeral head 16 shown in FIG. 1).

The glenoid component 300 includes a body 304 having a proximal or articulation surface 306. The articulation surface 306 is concave and adapted to engage the humeral component. The articulation surface 306 receives at least a portion of the humeral component within the concavity defined by the articulation surface 306.

Opposite the articulation surface 306, the body 304 includes a distal or scapula-facing surface 308. In some embodiments, the distal surface 308 supports one or more securing and/or stabilizing anchors, pins, or posts 310 which may have the same features and/or be arranged in the same manner as the anchors 110 described above.

The distal surface 308 of the glenoid component 300 is adapted to face the glenoid of the subject. In some embodiments, the glenoid may be an anatomical glenoid that has significant infero-posterior erosion and little or no supero-anterior erosion or such a glenoid that is at least partially prepared for receiving the glenoid component 300 (for example, by removing bone from the glenoid).

The distal surface 308 of the glenoid component 300 includes different portions that face different portions of the glenoid. Specifically, the distal surface 308 includes a base surface portion 316 that is adapted to face the supero-anterior portion of the glenoid. The distal surface 308 also includes an augmented surface portion 318 that is adapted to face the infero-posterior portion of the glenoid.

As shown most clearly in FIGS. 28-31, the augmented surface portion 318 is generally disposed further from the articulation surface 306 than the base surface portion 316. Stated another way, the body 304 of the glenoid component 300 is relatively thin between base surface portion 316 and the articulation surface 306. In contrast, the body 304 of the glenoid component 300 is relatively thick between the augmented surface portion 318 and the articulation surface 306.

In some embodiments, the base surface portion 316 is a convex surface. The base surface portion 316 may have a curved shape (for example, an arcuate shape) in a plane 320 that extends through the articulation surface 306, the base surface portion 316, and the augmented surface portion 318 (that is, a plane extending through the body 304 in a thickness direction and substantially bisecting each of the surfaces 306, 316, and 318; see FIG. 27). The base surface portion 316 may have a curved shape (for example, an arcuate shape) in a plane 322 that extends through the articulation surface 306 and the base surface portion 316 and is disposed apart from the augmented surface portion 318 (that is, a plane extending through the body 304 in a thickness direction, substantially bisecting the base surface portion 316, and not intersecting with the augmented surface portion 318; see FIG. 25).

In some embodiments, the augmented surface portion 318 is a convex surface. The augmented surface portion 318 may have a curved shape (for example, an arcuate shape) in the plane 320 (see FIG. 26). The augmented surface portion 318 may have a curved shape (for example, an arcuate shape) in a longitudinal plane 324 that extends through the articulation surface 306 and the augmented surface portion 318 and is disposed apart from the base surface portion 316 (that is, a plane extending through the body 304 in a thickness direction, substantially bisecting the augmented surface portion 318, and not intersecting with the base surface portion 316; see FIG. 25).

The augmented surface portion 318 and the base surface portion 316 intersect at an interface 326. In other words, the base surface portion 316 and the augmented surface portion 318 are connected by the interface 326. In some embodiments, the augmented surface portion 318 and the base surface portion 216 define an obtuse angle 328 at the interface 326 (see FIG. 19). More specifically, the base surface portion 316 has a first convex surface 316a, extending from the interface 326 to an anterior portion of the implant and adapted to face a first portion of the glenoid. The augmented surface portion 318 has a second convex surface 318a, extending from the interface 326 to at least one of a posterior portion, a supero-posterior portion, or an infero portion of the glenoid implant and adapted to face a second portion of the glenoid. Stated another way, the base surface portion 316 has a first, relatively-gradual slope toward the interface 326 and the augmented surface portion 318 has a second, relatively-inclined slope toward the interface 326. The first convex surface 316a has a first radius of curvature and the second convex surface 318a has a second radius of curvature. The first radius of curvature and the second radius of curvature may be the same or different. In some embodiments, the interface 326 substantially extends in a direction parallel to the planes 322 and 324 (see FIG. 25). That is, the interface3 may curve slightly relative to the planes 322 and 324 due to the shapes of the augmented surface portion 318 and the base surface portion 316.

FIGS. 32-39 illustrate an exemplary reaming device 400 according to embodiments of the present invention. The reaming device 400 may prepare, or remove, bone from the glenoid of the subject and facilitates subsequently implanting a glenoid component, such as one of the glenoid components 100, 200, or 300 described above.

Figure 33:
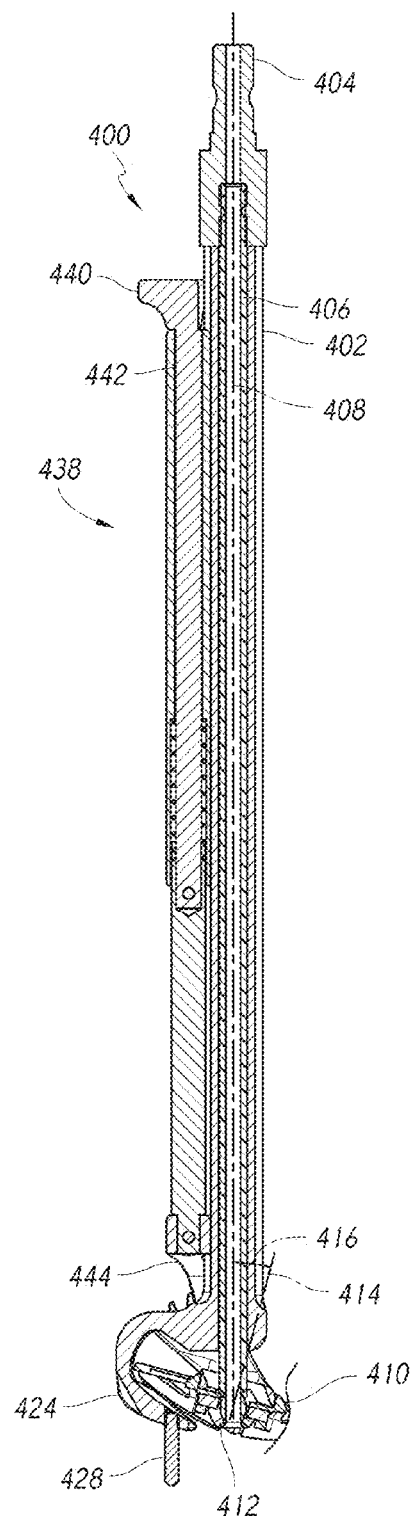
FIG. 33 is a rear longitudinal sectional view of the reaming device of FIG. 32.
Figure 34:
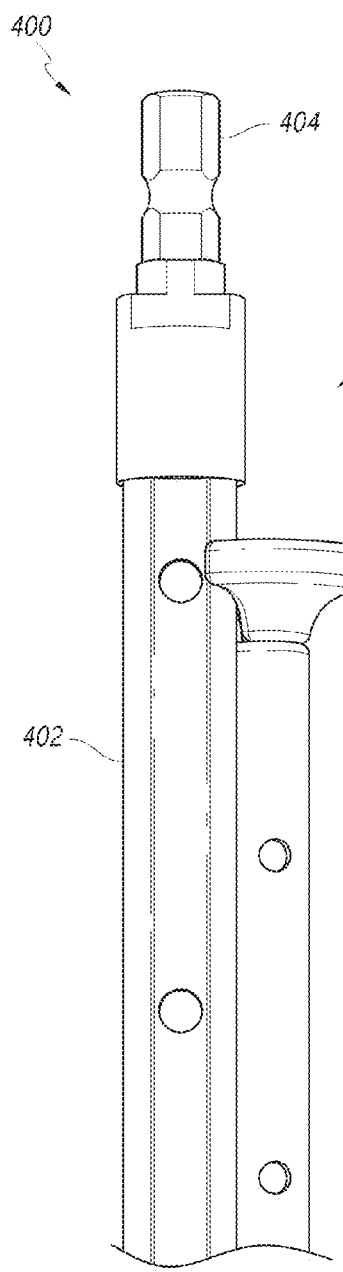
FIG. 34 is a detail front view of a proximal end of the reaming device of FIG. 32.
Figure 35:
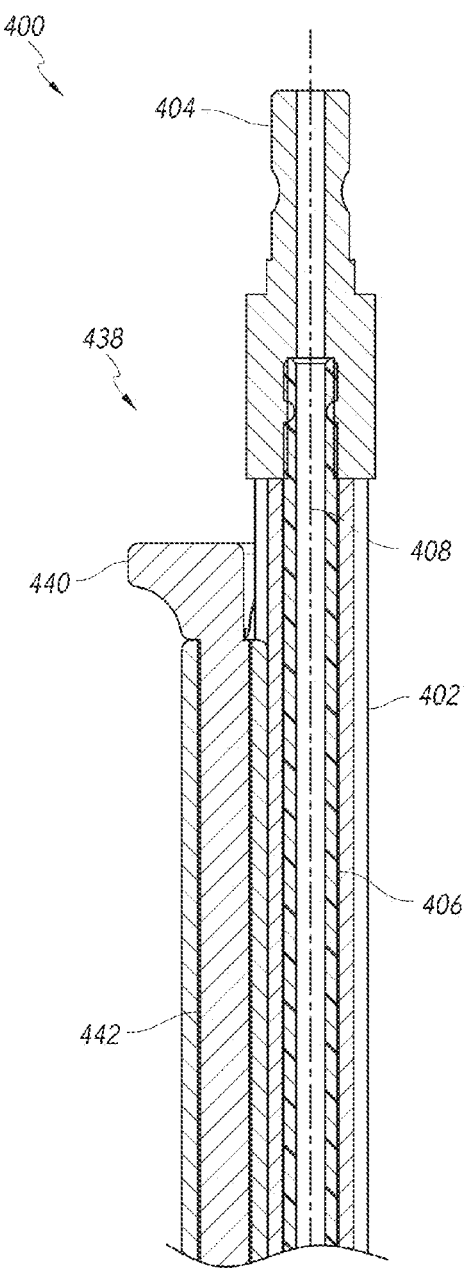
FIG. 35 is a detail rear longitudinal sectional view of the proximal end of the reaming device of FIG. 32.
Figure 36:
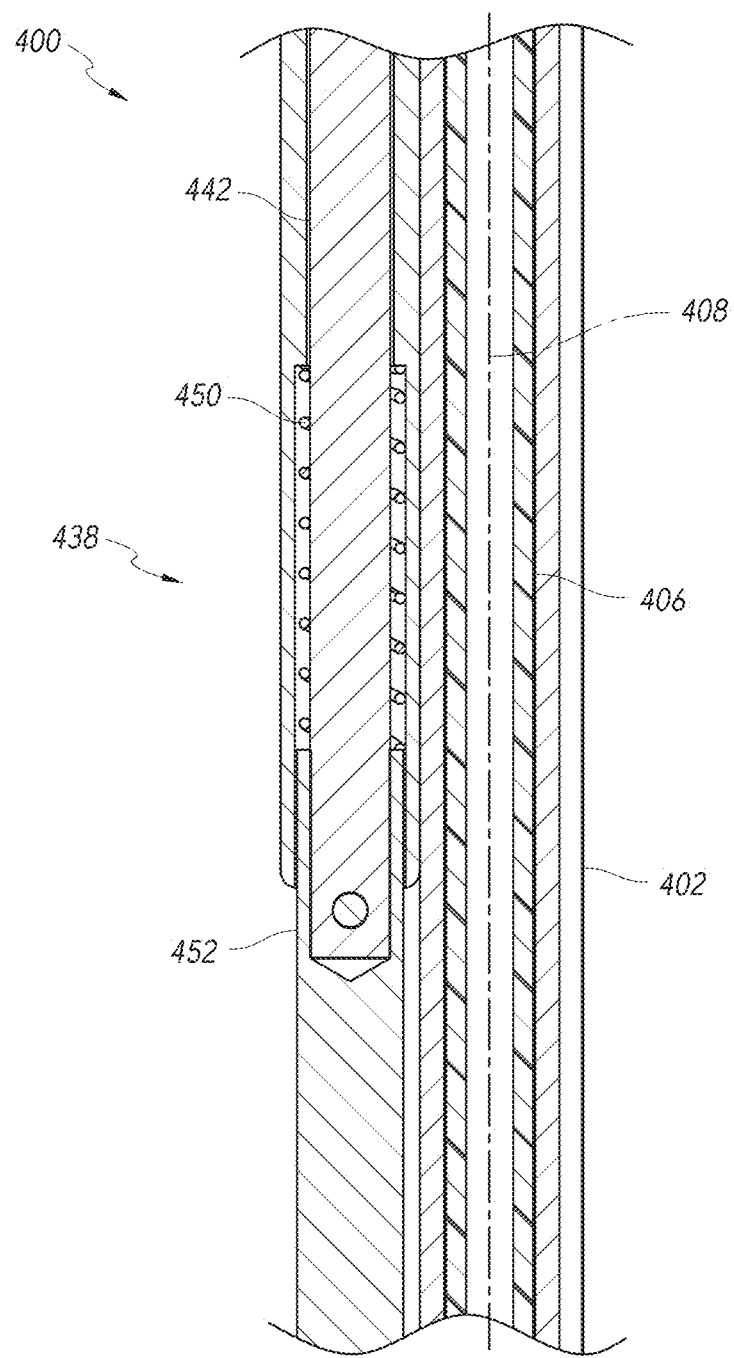
FIG. 36 is a detail rear longitudinal sectional view of an intermediate section of the reaming device of FIG. 32.
Figure 39:
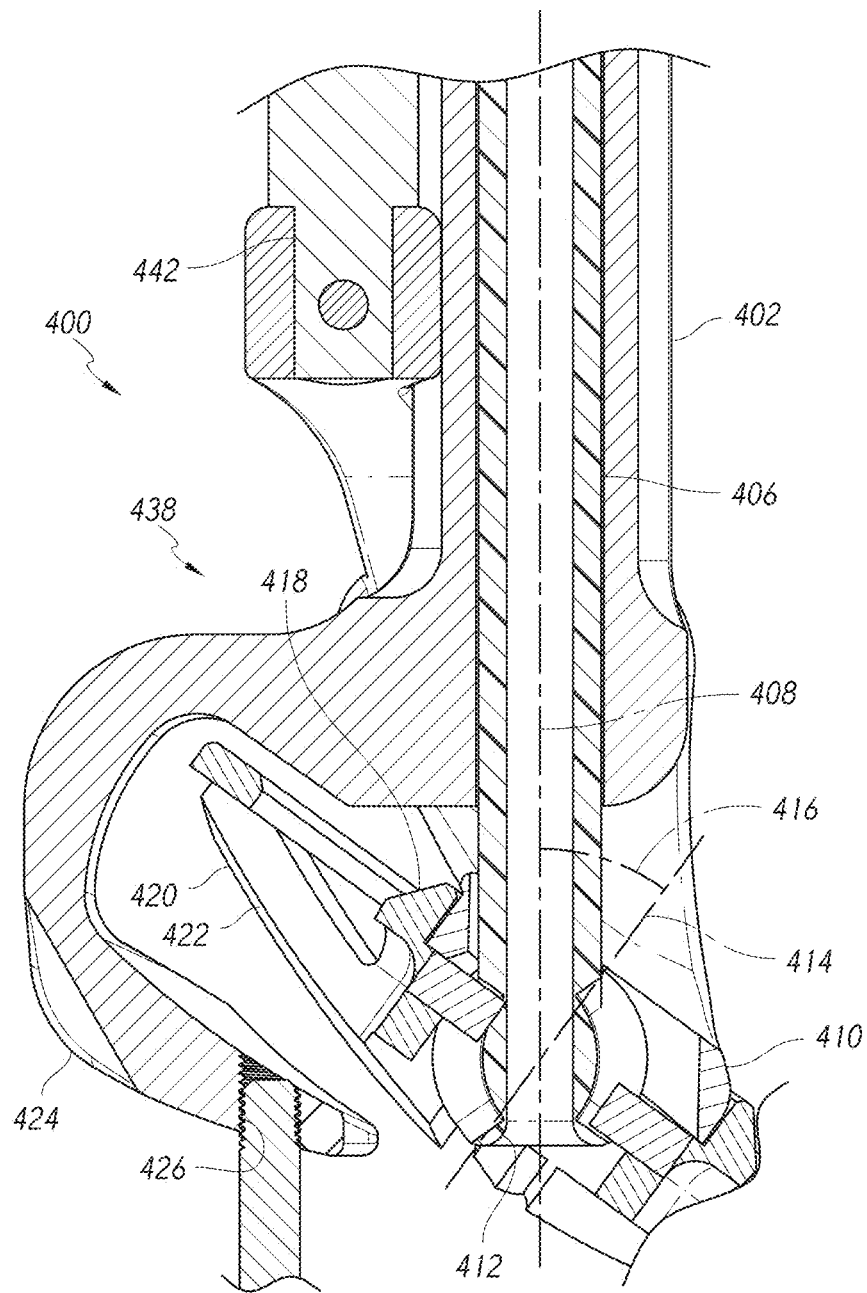
FIG. 39 is a detail rear longitudinal sectional view of the distal end of the reaming device of FIG. 32. The reaming head is shown in a second orientation.
Figure 40:
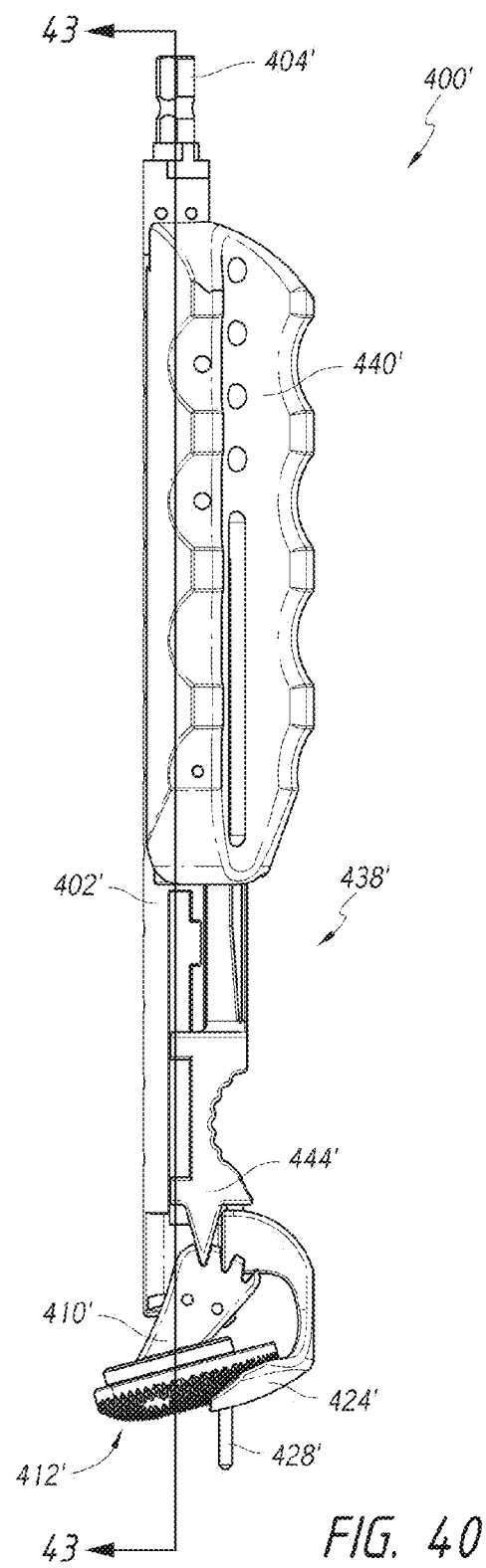
FIG. 40 illustrates a perspective view of another embodiment of a reaming device.
Figure 41:
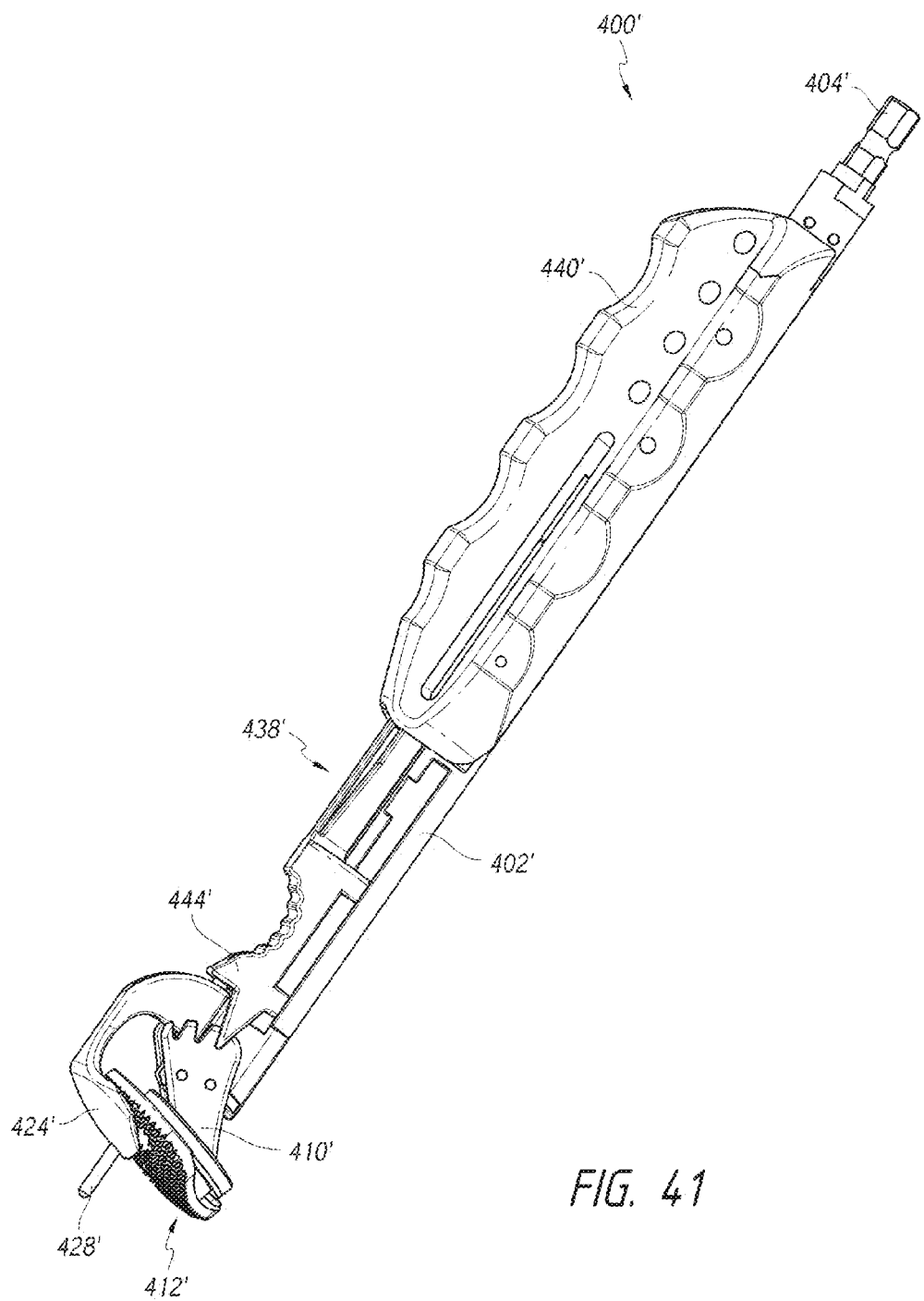
FIG. 41 illustrates another perspective view of the reaming device shown in FIG. 40.

The reaming device 400 includes a housing or frame 402 that may be manipulated by user (for example, a surgeon) to appropriately position the reaming device 400 relative to the glenoid of the subject. The frame 402 rotatably supports a drive coupling 404 at a proximal end. The drive coupling 404 is adapted to detachably couple to a prime mover (such as a hand-held drill or the like). The drive coupling 404 also connects to and rotatably drives a drive shaft 406 that is rotatably supported by the frame 402. The drive shaft 406 can be straight, such that the drive shaft 406 extends along and rotates about a drive axis 408. The drive shaft 406 transmits rotational motion from the proximal end of the reaming device 400 to an opposite, distal end of the device 400, for example because the distal end of the drive shaft 406 can be at least partially disposed within a reaming head 412. As shown in FIG. 33, the drive shaft 406 can be cannulated, so the reaming device 400 can be delivered over a guide pin (e.g., a K-wire). The cannulated drive shaft 406 can have a distal opening located adjacent to and/or distal of a distal-most portion of a reaming surface of the reaming head 412. The distal opening of the cannulated drive shaft 406 may be distal of an axis of angulation of the reaming head 412.

At the distal end of the device 400, the frame 402 includes a bearing or bushing 410 that can be adjusted to select the angle of a reaming axis 414 of the reaming head 412, such that the reaming axis 414 can be parallel or non-parallel to the drive shaft axis 408 at a distal end of the drive shaft 406. The bearing 410 facilitates adjustment of the angle of the reaming head 412, such that when the drive shaft 406 rotates the reaming head 412, the reaming head 412 engages the bone asymmetrically relative to an axis extending longitudinally through the distal end of the draft shaft 406 to ream the bone asymmetrically relative to the axis. The reaming axis 414 intersects with and can be disposed non-parallel to the drive axis 408 of the shaft 406, for example within the reaming head 412. As such, the reaming head 412 may be referred to as "inclined" or "sloped" relative to the frame 402 in some configurations. In some embodiments and as described in further detail below, the bearing 410 may be pivotally supported by the remainder of the frame 402 about an axis 415 that is substantially perpendicular to both the reaming axis 414 and the drive axis 408. As a result, an angle 416 between the reaming axis 414 and the drive axis 408 may be selectively adjusted between two or more orientations (e.g., two orientations, three orientations, four orientations, or more). For example, the reaming device 400 can have a first configuration to rotate the reaming head 412 about a first reaming axis when the reaming head 412 is in a first orientation and a second configuration to rotate the reaming head 412 about a second reaming axis when the reaming head 412 is in a second orientation. For example, the first reaming axis can be substantially aligned with the drive shaft axis 408, and the second reaming axis can be at a non-parallel angle relative to the drive shaft axis 408. As another example, the first reaming axis can be at a first non-parallel angle relative to the drive shaft axis (e.g., about 8 degrees), and the second reaming axis can be at a second non-parallel angle relative to the drive shaft axis 408 (e.g., about 12 degrees). Unlike traditional approaches to reaming (see, e.g., FIGS. 5A-7B), the ability to adjust the angle 416 between the reaming axis 414 and the drive axis 408 enables the user to avoid removing excess bone, e.g., to only remove the necessary portions of the bone.

The reaming head 412 includes a base 418 (see FIGS. 37 and 38) that connects to the bearing 410. The base 418 also supports one or more reaming elements 420, each of which includes a reaming edge or surface 422. When the reaming head 412 rotates, the reaming edges 422 may engage and prepare bone (that is, shape the bone) for subsequently receiving a glenoid component, such as one of the glenoid components 100, 200, or 300 described above. In some embodiments, each of the reaming edges 422 has an outwardly curved shape (for example, an arcuate shape) such that the reaming head 412 forms a concave surface in the bone for subsequently receiving the glenoid component.

The reaming device 400 may include a guard or guard member 424 removably coupled to a distal portion of the frame 402. The guard member 424 can include a generally C-shaped member such that a distal portion of the guard member 424 is disposed distal to the reaming head 412. The guard member 424 can be shaped such that a plane extending through the distal portion of the guard member 424 is at an angle relative to the drive axis 408. As such, the guard 424 inhibits the upper portion of the reaming head 412 from engaging bone during a reaming procedure. The guard 424 is disposed apart from an opposite lower portion of the reaming head 412 (not shown). As such, the lower portion of the reaming head 412 engages and prepares bone during a reaming procedure. The guard 424 may include an attachment element or feature (for example, a threaded hole 426) that detachably mounts a guide post 428. The guide post 428 may be used to guide advancement of the reaming device 400 during a reaming procedure.

The reaming head 412 is rotatably driven by the drive shaft 406 through a coupling mechanism 430, e.g., a pivot coupling (see FIG. 38). The coupling mechanism 430 can be a separate component from the reaming head 412 that is disposed laterally between the reaming head 412 and the distal end of the drive shaft 406. Although, in other embodiments, the coupling mechanism 430 may be a component of the reaming head 412.

The coupling mechanism 430 facilitates rotation of the drive shaft 406 and/or the reaming head 412 about the reaming axis 414. The reaming axis 414 may be non-parallel to the drive shaft axis 408. In some embodiments and as shown in the figures, the coupling mechanism 430 includes a generally sphere-shaped element 432 at the distal end of the drive shaft 406. The sphere-shaped element 432 includes one or more slots 434. The slots 434 may have arcuate shapes and may generally extend in the direction of the drive axis 408. Each slot 434 translatably receives a post or pin 436 supported by reaming head 412. The posts 436 and the reaming head 412 are rotatably driven by the drive shaft 406 due to engagement between the sphere-shaped element 432 and the posts 436. As the reaming head 412 rotates, the posts 436 move upwardly and downwardly in the slots 434, once per revolution, due to the non-parallel arrangement of the reaming axis 414 and the drive axis 408.

In some embodiments, the reaming device 400 includes a locking mechanism 438 that couples the reaming head 412 to the frame 402. A user may move the locking mechanism 438 between a locked position and an unlocked position. In the locked position, the locking mechanism 438 inhibits adjustment of the angle 416 between the drive axis 408 and the reaming axis 414. In the unlocked position, the locking mechanism 438 permits adjustment of the angle between the drive axis 408 and the reaming axis 414.

In some embodiments and as shown in the figures, the locking mechanism 438 includes a handle 440 that may be manipulated by the user to move between the locked position and the unlocked position. Specifically, the handle 440 may be displaced in a direction that is substantially perpendicular to the drive axis 408. The handle 440 connects to a rod 442 that is translatably supported by the frame 402. Opposite the handle 440, the rod 442 connects to a tooth 444. The tooth 444 is removably received in one of a plurality of notches 446 (see FIG. 37) defined by the bearing 410. The bearing 410 may include three notches 446, although the bearing 410 may alternatively include different numbers of notches 446. In any case, each notch 446 defines an angle, or orientation, at which the reaming axis 414, and the reaming head 412, may be disposed relative to the drive axis 408. The reaming axis 414 and the reaming head 412 may be disposed, for example, at angles of 15 degrees (see FIGS. 37 and 38), 25 degrees (not shown), and 35 degrees (see FIG. 39) relative to the drive axis 408.

In the locked position, the tooth 444 is received in one of the notches 446 to inhibit adjustment of the angle 416 between the drive axis 408 and the reaming axis 414. To move to the unlocked position, the user may pull the handle 440 toward the proximal end of the reaming device 400. In the unlocked position, the tooth 444 is disposed apart from the notches 446. As such, the user may pivot the bearing 410 about the axis 415 to adjust the angle 416 between the drive axis 408 and the reaming axis 414. After pivoting the bearing 410, the locking mechanism 438 may be moved to the locked position.

In some embodiments, the locking mechanism 438 includes a biasing element that biases the locking mechanism 438 toward the locked position. The biasing element may be a compression spring 450 (see FIG. 36) that is carried within the frame 402. When the handle 440 is pulled to move the locking mechanism 438 to the unlocked position, the spring 450 is compressed between the frame 402 and an enlarged diameter section 452 of the rod 442. As such, the user may release the handle 440 to permit the spring 450 to return the locking mechanism 438 to the locked position. Specifically, the spring 450 displaces the rod 442 to cause the tooth 444 to engage one of the notches 446.

FIGS. 40-44 illustrate an exemplary reaming device 400' similar to the reaming device 400 discussed above except as described differently below. Accordingly, numerals used to identify features of the reaming device 400 include an apostrophe (') to identify like features of the reaming device 400'. The reaming device 400' includes a reaming head 412' that rotates about a reaming axis 414' (see FIG. 43). The reaming axis 414' intersects with and is non-parallel to the drive axis 408' of a drive shaft 406' (see FIG. 43). The angle between the reaming axis 414' and the drive axis 408' may be selectively adjusted to enable the user to reduce the removal of bone that does not need to be removed, e.g., to only remove the portions of the bone that need to be removed to insert any of the glenoid components described herein.

Figure 42:
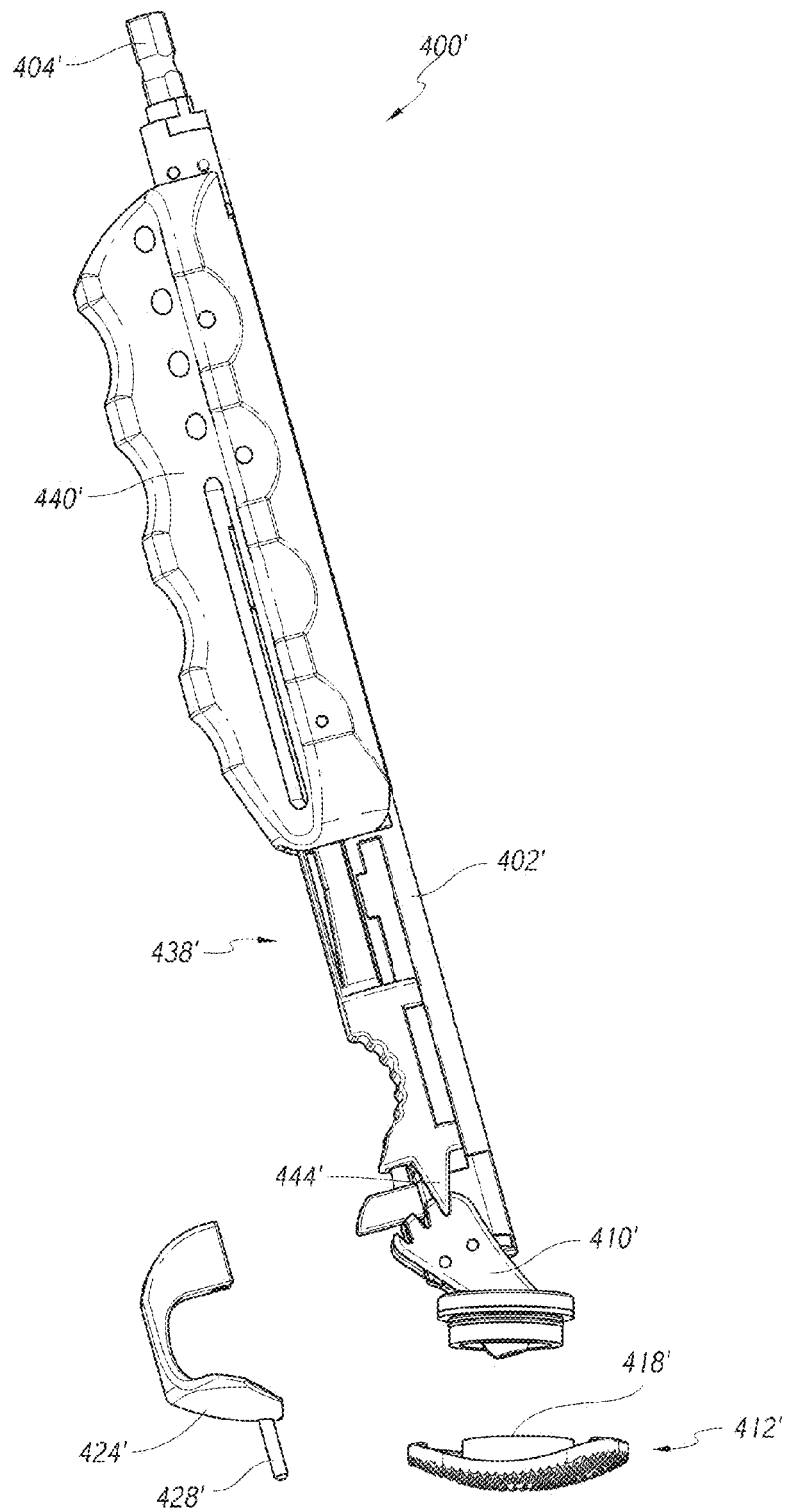
FIG. 42 illustrates a partial-exploded view of the reaming device shown in FIG. 40.
Figure 44:
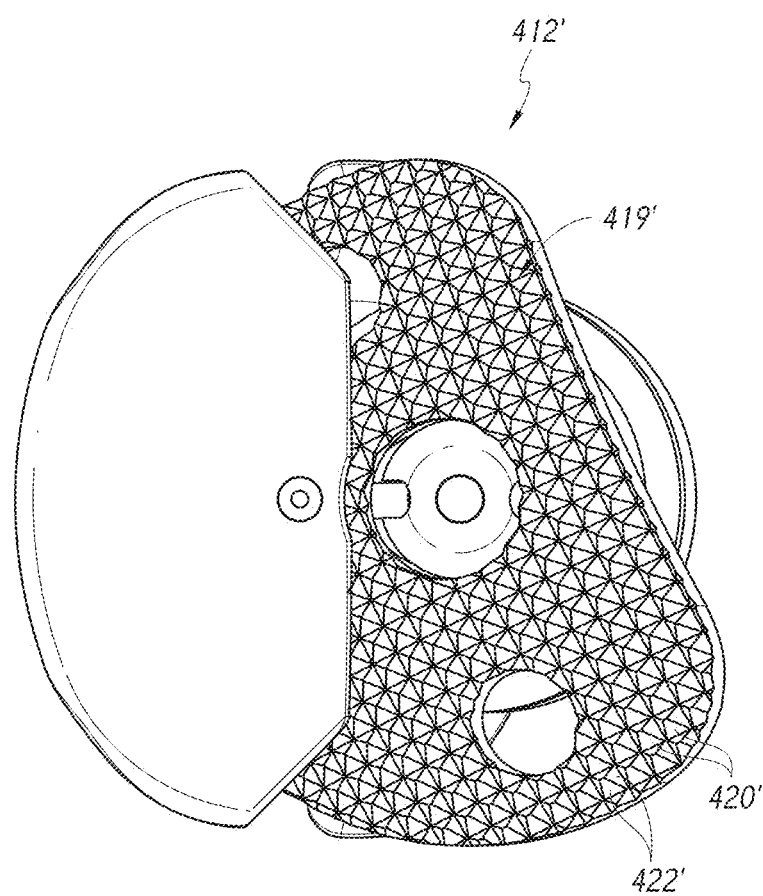
FIG. 44 illustrates a bottom view of the reaming device shown in FIG. 40.

FIG. 42 shows that the reaming head 412' can include a base 418' that connects to the bearing 410'. FIG. 44 shows that the base 418' has a reaming surface 419' that can remove bone. The reaming surface 419' can include one or more reaming elements 420', each of which includes a reaming edge or surface 422'. Each reaming element 420' can share an edge with another reaming element 420'. For example, the reaming surface 419' can include a number of adjacent rows of reaming elements 420'. When the reaming head 412' rotates, the reaming edges 422' may engage and prepare bone (that is, shape the bone) for subsequently receiving a glenoid component, such as one of the glenoid components 100, 200, or 300 described above. In some embodiments, each of the reaming elements 420' can be disposed along an outwardly oriented surface (for example, an arcuate or convex shape) such that the reaming head 412' forms a concave surface in the bone for subsequently receiving the glenoid component.

Figure 43:
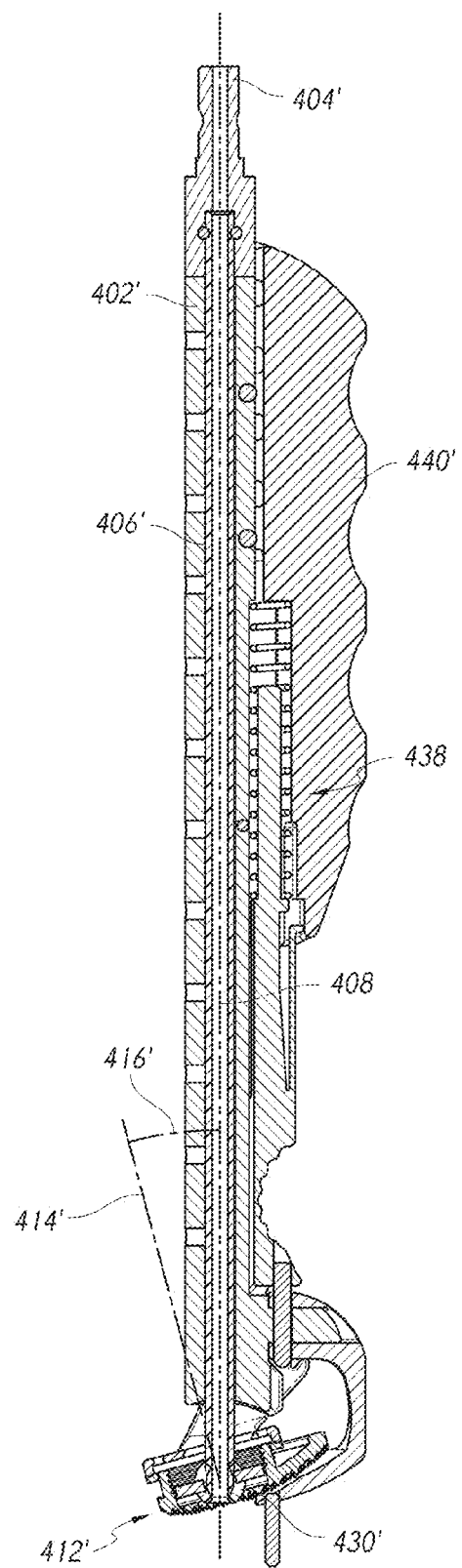
FIG. 43 illustrates a cross-section of the reaming device shown in FIG. 40 taken through line 43-43.

The reaming head 412' is rotatably driven by the drive shaft 406 through a coupling mechanism 430', e.g., a pivot coupling (see FIG. 43). The coupling mechanism 430' facilitates rotation of the drive shaft 406' and the reaming head 412' about non-parallel axes (that is, the drive axis 408' and the reaming axis 414').

Figure 45:
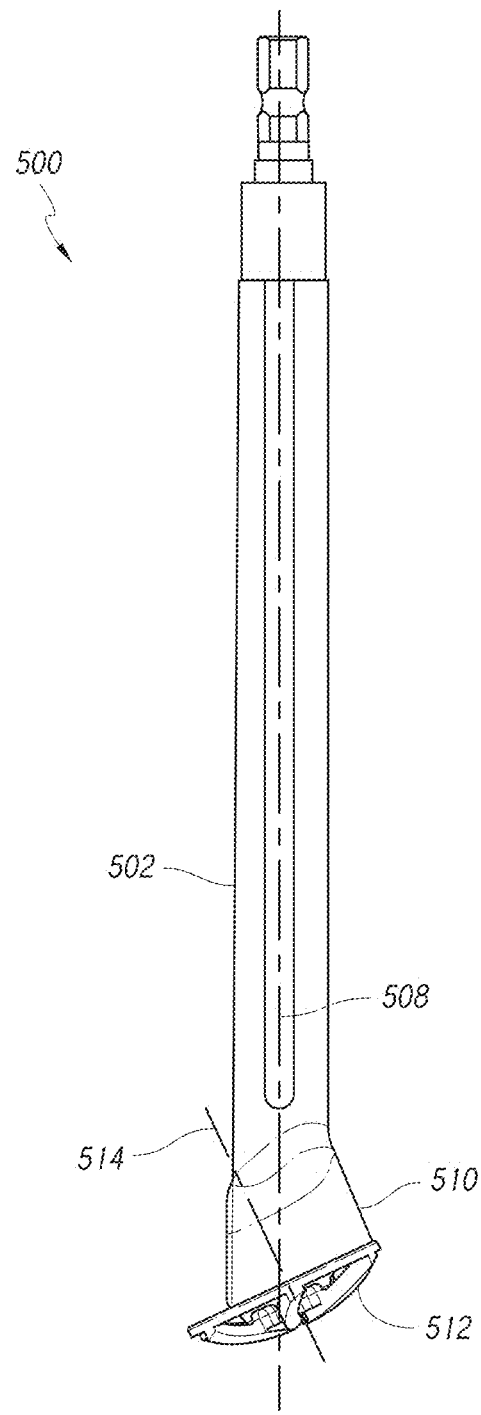
FIG. 45 is a front view of a reaming device according to embodiments of the present invention.
Figure 46:
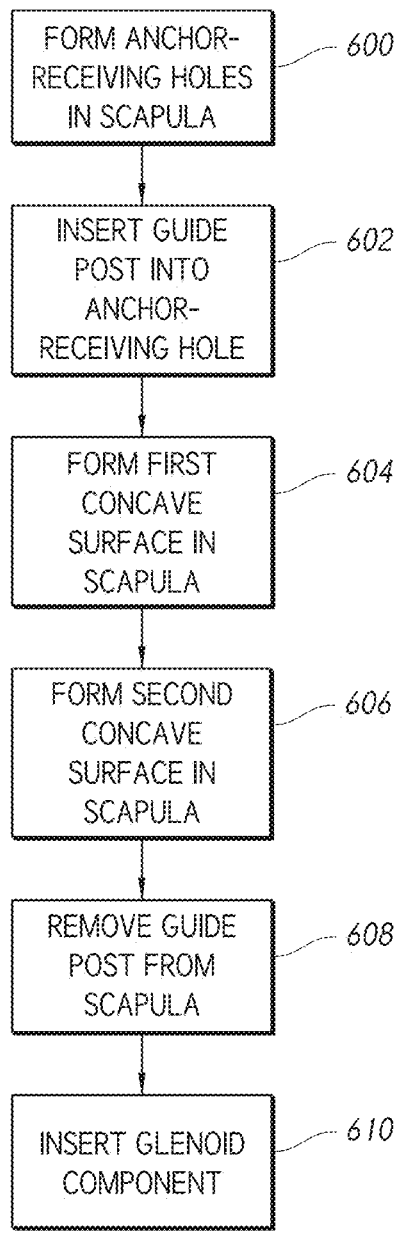
FIG. 46 is a flowchart of an exemplary method for coupling a glenoid component to a scapula of a subject according to embodiments of the present invention.
Figure 47:
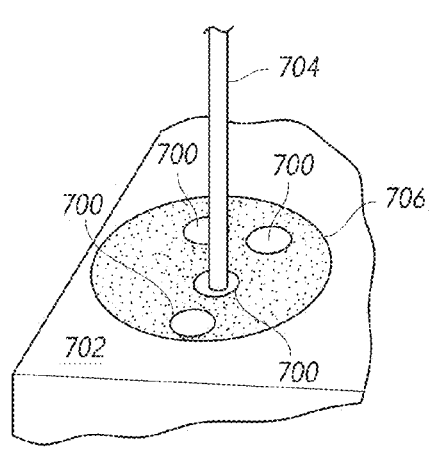
FIG. 47 illustrates forming a first concave surface in a scapula of a subject.

FIG. 45 illustrates an exemplary reaming device 500 according to embodiments of the present invention. The reaming device 500 may be generally similar to the reaming device 400 described above. That is, the reaming device 500 includes a reaming head 512 that rotates about a reaming axis 514. The reaming axis 514 intersects with and is non-parallel to the drive axis 508 of a drive shaft (not shown). However, a bearing 510 that rotatably mounts the reaming head 512 is fixedly connected to a remainder of the device frame 502. For example, the bearing 510 may be monolithically formed (for example, formed from or as a single piece of material) with the remainder of the frame 502.

FIGS. 46-51 illustrate an exemplary method for coupling a glenoid component, such as one of the glenoid components 100, 200, or 300 described above, to a scapula of a subject according to embodiments of the present invention. At block 600, one or more anchor-receiving holes 700 are formed in the scapula 702 of the subject (see FIG. 47). At block 602, a guide pin 704 is inserted into one of the anchor-receiving holes 700. At block 604, a first concave surface 706 is formed in the scapula 702 of the subject. In some embodiments, the surface 706 may be formed by using a reaming device that has parallel drive and reaming axes (e.g., having a reaming axis in a direction similar to FIGS. 5A-5C). In some embodiments, the surface 706 may be formed by using the reaming device 400 described above. The reaming head 412 may be oriented at a relatively shallow angle (for example, 15 degrees). In some embodiments, the surface 706 may be formed at a portion of the glenoid that has experienced little to no erosion, such as an anterior portion, a supero-anterior portion, or an infero-anterior portion.

Figure 48:
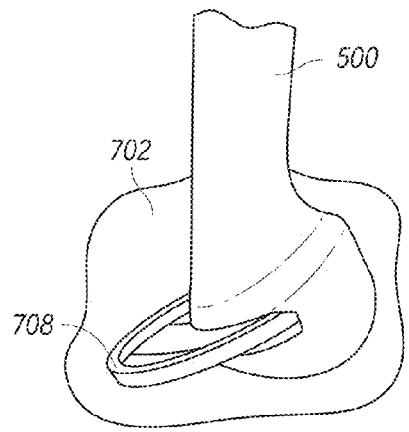
FIGS. 48 and 49 illustrate forming a second concave surface in a scapula of a subject.
Figure 49:
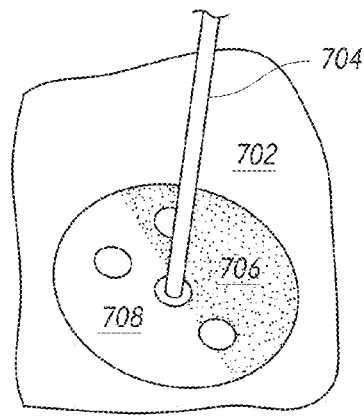
Figure 50:
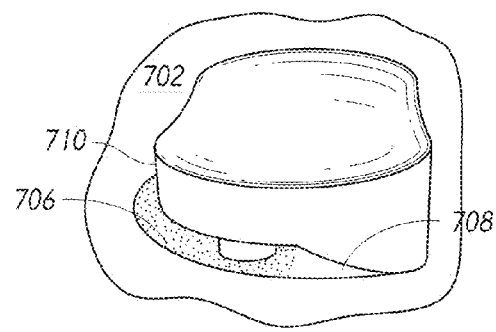
FIGS. 50 and 51 illustrate connecting a glenoid component to the scapula of a subject.
Figure 51:
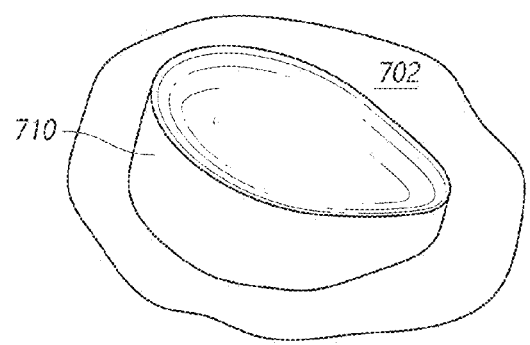

At block 606, a second concave surface 708 is formed in the scapula 702 of the subject (see FIGS. 48 and 49). In some embodiments, the surface 708 may be formed by using one of the reaming devices 400 or 500 described above. In some embodiments, the reaming head 412 may be oriented at a relatively steep angle (for example, 35 degrees). In some embodiments, the second concave surface 708 may be formed at a portion of the glenoid that has experienced a significant amount of erosion, such as a posterior portion, a supero-posterior portion, or an infero-posterior portion.

At block 608, the guide pin 704 is removed from the scapula 702. At block 610, a glenoid component 710 is connected to the scapula 702 (see FIGS. 50 and 51). If the glenoid component 710 is, for example, the glenoid component 100 described above, the base surface portion 116 may face the first concave surface 706 and the augmented surface portion 118 may face the second concave surface 708.

The glenoid components, reaming instruments, and methods described above may be subjected to various other modifications. For example, in some embodiments the glenoid components described above may have an offset center as described in U.S. Patent App. Pub. 2011/0125273, published on May 26, 2011, which is hereby incorporated by reference in its entirety. In some embodiments, the center of the glenoid-facing surface is offset from an axis of symmetry of the articulation surface. In some embodiments, the interface between the base surface portion and the augmented surface portion is offset from the barycentre of the articulation surface.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

As used herein, the relative terms "proximal" and "distal" when describing the reaming device shall be defined from the perspective of the reaming device. Thus, proximal refers to the direction of the drive coupling of the reaming device and distal refers to the direction of the reaming head.

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments.

For purposes of this disclosure, certain aspects, advantages, and novel features are described herein. It is to be understood that not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Moreover, while illustrative embodiments have been described herein, the scope of any and all embodiments having equivalent elements, modifications, omissions, combinations (e.g., of aspects across various embodiments), adaptations and/or alterations as would be appreciated by those in the art based on the present disclosure. The limitations in the claims are to be interpreted broadly based on the language employed in the claims and not limited to the examples described in the present specification or during the prosecution of the application, which examples are to be construed as non-exclusive. Further, the actions of the disclosed processes and methods may be modified in any manner, including by reordering actions and/or inserting additional actions and/or deleting actions. It is intended, therefore, that the specification and examples be considered as illustrative only, with a true scope and spirit being indicated by the claims and their full scope of equivalents.

Any methods disclosed herein need not be performed in the order recited. The methods disclosed herein include certain actions taken by a practitioner; however, they can also include any third-party instruction of those actions, either expressly or by implication. For example, actions such as "forming anchor-receiving holes in scapula" include "instructing formation of anchor-receiving holes in scapula."

EXAMPLE EMBODIMENTS

The following example embodiments identify some possible permutations of combinations of features disclosed herein, although other permutations of combinations of features are also possible.

1. A glenoid component for coupling to a scapula of a subject, the glenoid component comprising:
   a body including an articulation surface adapted to articulate with a humeral component, and the body further including a distal surface adapted to face a glenoid of the scapula, the distal surface including:
   a base surface portion including a first convex surface adapted to face a first portion of the glenoid; and
   an augmented surface portion including a second convex surface adapted to face a second portion of the glenoid;
   wherein the base surface portion and the augmented surface portion are connected therebetween by an interface.

2. The glenoid component of Embodiment 1, wherein the interface is substantially planar.

3. The glenoid component of Embodiment 1 or 2, wherein the first convex surface has a first radius of curvature.

4. The glenoid component of Embodiment 3, wherein the second convex surface has a second radius of curvature.

5. The glenoid component of Embodiment 4, wherein the first radius of curvature is the same as the second radius of curvature.

6. The glenoid component of any one of the preceding Embodiments, wherein the first convex surface extends from the interface to an anterior portion of the glenoid component.

7. The glenoid component of any one of the preceding Embodiments, wherein the second convex surface extends from the interface to at least one of a posterior portion, a supero-posterior portion or an infero-posterior portion of the glenoid component.

8. The glenoid component of any one of the preceding Embodiments, wherein the augmented surface portion has a curved shape in a plane extending through the articulation surface, the base surface portion, and the augmented surface portion.

9. The glenoid component of any one of Embodiments 1 to 7, wherein the augmented surface portion has a curved shape in a plane extending through the articulation surface and the augmented surface portion, and the plane is disposed apart from the base surface portion.

10. The glenoid component of any one of the preceding Embodiments, further comprising a plurality of anchors extending from the distal surface and adapted to be received by the scapula.

11. The glenoid component of any one of the preceding Embodiments, wherein the augmented surface portion and the base portion define an obtuse angle at the interface.

12. A device for removing bone from a glenoid of a subject, the device comprising:
   a frame adapted to be manipulated by a user;
   a reaming head comprising a reaming surface;
   a drive shaft rotatably supported by and extending through the frame and having a distal end coupled with the reaming head, the drive shaft rotatable about a drive shaft axis at the distal end; and
   a bearing supported by the frame, the bearing capable of providing a rotational axis of the reaming head that is non-parallel to the drive shaft axis at the distal end.

13. The device of Embodiment 12, wherein the drive shaft is substantially straight and has a distal end at least partially disposed within the reaming head.

14. The device of Embodiment 12 or 13, further comprising a pivot coupling disposed laterally between the reaming head and the distal end of the drive shaft.

15. The device of any one of Embodiments 12 to 14, wherein an intersection of the rotational axis of the reamer and the drive shaft axis is disposed within the reaming head.

16. The device of any one of Embodiments 12 to 15, wherein, in operation, the device is configured such that when the drive shaft rotates the reaming head, the reaming head engages the bone asymmetrically relative to an axis extending longitudinally through the distal end of the drive shaft to ream the bone asymmetrically relative to the axis.

17. A device for removing bone from a glenoid of a subject, the device comprising:
   a frame adapted to be manipulated by a user;
   a reaming head comprising a reaming surface; and
   a drive shaft rotatably supported by and extending through the frame and having a distal end coupled with the reaming head, the drive shaft rotatable about a drive shaft axis; and
   a guard member coupled to a distal portion of the frame, the guard member configured to inhibit a portion of the reaming surface from engaging bone.

18. The device of Embodiment 17, wherein the guard member is generally C-shaped.

19. The device of Embodiment 17 or 18, wherein a distal portion of the guard member is distal to the reaming head.

20. The device of Embodiment 19, wherein the distal portion of the guard member is spaced apart from the reaming surface.

21. The device of any one of Embodiments 17 to 20, wherein a distal portion of the guard member is configured to be detachably mounted to a guide post.

22. The device of Embodiment 21, wherein the distal portion of the guard member comprises an attachment feature configured to be detachably mounted to the guide post.

23. The device of any one of Embodiments 17 to 22, wherein the reaming surface comprises a plurality of reaming elements configured to shape bone.

24. The device of Embodiment 23, wherein each reaming element shares an edge with another reaming element.

25. The device of Embodiment 23 or 24, wherein each reaming element comprises a curved reaming surface.

26. A device for removing bone from a glenoid of a subject, the device comprising:
   a frame adapted to be manipulated by a user;
   a reaming head comprising a reaming surface;
   a cannulated drive shaft rotatably supported by and extending at least partially through the frame and having a distal end coupled with the reaming head, the drive shaft rotatable about a drive shaft axis; and
   wherein the device has a first configuration to rotate the reaming head about a first reaming axis when the reaming head is in a first orientation; and
   wherein the device has a second configuration to rotate the reaming head about a second reaming axis when the reaming head is in a second orientation.

27. The device of Embodiment 26, wherein the cannulated drive shaft has a distal opening located adjacent to a distal-most portion of the reaming surface.

28. The device of Embodiment 26 or 27, wherein the cannulated drive shaft has a distal opening located distal of a distal-most portion of the reaming surface.

29. The device of any one of Embodiments 26 to 28, wherein the cannulated drive shaft has a distal opening located distal of an axis of angulation of reaming head.

30. The device of any one of Embodiments 26 to 29, wherein the reaming axis and the drive shaft axis intersect within the reaming head when a non-zero angle is provided between the reaming axis and the drive shaft axis.

31. A kit comprising:
the device of any one of Embodiments 26 to 30; and
a guide pin having a first end configured to be disposed in bone and a second end configured to be received within the cannulated drive shaft.

What is claimed is:

1. A device for removing bone from a glenoid of a subject, the device comprising:
a frame adapted to be manipulated by a user;
a reaming head comprising a reaming surface;
a drive shaft rotatably supported by and extending through the frame and having a distal end at least partially disposed within the reaming head, the drive shaft rotatable about a drive shaft axis at the distal end; and
a bearing supported by the frame, the bearing capable of providing a rotational axis of the reaming head between a minimum angle defined between the rotational axis and the drive shaft axis and a maximum angle defined between the rotational axis and the drive shaft axis;
wherein the reaming head is rotated about the rotational axis upon rotation of the drive shaft relative to the frame and about the drive shaft axis when the device is operated to remove bone from the glenoid; and
wherein when the bearing provides the maximum angle, a non-zero angle is defined between the rotational axis and the drive shaft axis, an intersection of the rotational axis and the drive shaft axis is disposed within the reaming head.

2. The device of claim 1, wherein the drive shaft is straight when the non-zero angle is defined between the rotational axis and the drive shaft axis.

3. The device of claim 1, further comprising a pivot coupling disposed laterally between the reaming head and the distal end of the drive shaft.

4. The device of claim 1, wherein, in operation, the device is configured such that when the drive shaft rotates the reaming head, the reaming head engages the bone asymmetrically relative to an axis extending longitudinally through the distal end of the drive shaft to ream the bone asymmetrically relative to the axis.

5. The device of claim 1, further comprising:
a guard member having a distal portion and a proximal portion, the proximal portion coupled to a distal portion of the frame, the guard member configured to inhibit a portion of the reaming surface from engaging bone,
wherein the guard member extends around a lateral edge of the reaming head so that the distal portion of the guard member is disposed distal to at least a portion of a distal face of the reaming head, and
wherein the distal portion of the guard member is at least partially positioned radially inward of the lateral edge of the reaming head.

6. The device of claim 5, wherein the guard member is generally C-shaped.

7. The device of claim 5, wherein the distal portion of the guard member is configured to be detachably mounted to a guide post.

8. The device of claim 7, wherein the distal portion of the guard member comprises an attachment feature configured to be detachably mounted to the guide post.

9. The device of claim 5, wherein the reaming surface comprises a plurality of reaming elements, each reaming element sharing an edge with another reaming element.

10. The device of claim 5, wherein the reaming surface comprises a plurality of reaming elements, each reaming element comprising a curved reaming surface.

11. A device for removing bone from a glenoid of a subject, the device comprising:
a frame adapted to be manipulated by a user;
a reaming head comprising a reaming surface;
a cannulated drive shaft rotatably supported by and extending at least partially through the frame, the drive shaft rotatable about a drive shaft axis extending through a distal end of the cannulated drive shaft;
a bearing supported by the frame and configured to provide a first configuration and a second configuration, the distal end of the cannulated drive shaft being positioned distal of the bearing,
wherein in the first configuration, the reaming head is configured to rotate about a first reaming axis having a first orientation relative to the drive shaft axis; and
wherein in the second configuration, the reaming head is configured to rotate about a second reaming axis having a second orientation relative to the drive shaft axis, the second orientation being different from the first orientation.

12. The device of claim 11, wherein the cannulated drive shaft has a distal opening located adjacent to a distal-most portion of the reaming surface.

13. The device of claim 11, wherein the cannulated drive shaft has a distal opening located distal of a distal-most portion of the reaming surface.

14. The device of claim 11, wherein the cannulated drive shaft has a distal opening located distal of an axis of angulation of reaming head.

15. The device of claim 11, wherein the reaming axis and the drive shaft axis intersect within the reaming head when a non-zero angle is provided between the reaming axis and the drive shaft axis.

16. The device of claim 11, wherein the cannulated drive shaft is straight in the first configuration and the second configuration.

17. The device of claim 11, wherein the distal end of the cannulated draft shaft is coupled with the reaming head.

18. The device of claim 11, further comprising a pivot coupling disposed laterally between the reaming head and the distal end of the cannulated drive shaft.

19. A kit comprising:
the device of claim 11; and
a guide pin having a first end configured to be disposed in bone and a second end configured to be received within the cannulated drive shaft.

20. A device for removing bone from a glenoid of a subject, the device comprising:
a frame adapted to be manipulated by a user;
a reaming head comprising a reaming surface;
a drive shaft rotatably supported by and extending through the frame, the drive shaft rotatable about a drive shaft axis; and
a bearing supported by the frame, the bearing capable of providing a rotational axis of the reaming head, a distal end of the drive shaft being positioned distal of the bearing;
wherein the reaming head is rotated about the rotational axis upon rotation of the drive shaft relative to the frame and about the drive shaft axis when the device is operated to remove bone from the glenoid; and wherein when a non-zero angle is defined between the rotational axis and the drive shaft axis, an intersection of the rotational axis and the drive shaft axis is disposed within the reaming head.

21. The device of claim 20, wherein the drive shaft is straight when the non-zero angle is defined between the rotational axis and the drive shaft axis.

22. The device of claim 20, further comprising a pivot coupling disposed laterally between the reaming head and the distal end of the drive shaft.

23. The device of claim 20, wherein, in operation, the device is configured such that when the drive shaft rotates the reaming head, the reaming head engages the bone asymmetrically relative to an axis extending longitudinally through the distal end of the drive shaft to ream the bone asymmetrically relative to the axis.

24. The device of claim 20, wherein the distal end of the cannulated draft shaft is coupled with the reaming head.

\* \* \* \* \*